United States Patent
Kim et al.

(10) Patent No.: US 8,293,774 B2
(45) Date of Patent: Oct. 23, 2012

(54) OPTICALLY ACTIVE (R)-ARYLOXYPROPIONIC ACID AMIDES AND HERBICIDAL COMPOSITION COMPRISING SAME

(75) Inventors: Joo-kyung Kim, Gyeongju-si (KR); Dong-hoo Kim, Gyeongju-si (KR); Hyung-ho Kim, Daejeon (KR); Kyung-hyun Kim, Gyeongju-si (KR); Cheol-su Yoon, Gyeongju-si (KR); In-cheon Hwang, Gyeongju-si (KR)

(73) Assignee: Kyung Nong Corporation, Seoul (KR)

( * ) Notice: Subject to any disclaimer, the term of this patent is extended or adjusted under 35 U.S.C. 154(b) by 0 days.

(21) Appl. No.: 12/667,506

(22) PCT Filed: Jul. 2, 2008

(86) PCT No.: PCT/KR2008/003899
§ 371 (c)(1),
(2), (4) Date: Jun. 14, 2010

(87) PCT Pub. No.: WO2009/005297
PCT Pub. Date: Jan. 8, 2009

(65) Prior Publication Data
US 2010/0279871 A1 Nov. 4, 2010

(30) Foreign Application Priority Data
Jul. 3, 2007 (KR) .................. 10-2007-0066270

(51) Int. Cl.
*A61K 31/428* (2006.01)
*A61K 31/423* (2006.01)
*A61K 31/4168* (2006.01)
*C07D 417/12* (2006.01)
*C07D 277/82* (2006.01)
*C07D 263/58* (2006.01)
*C07D 235/24* (2006.01)

(52) U.S. Cl. ........ 514/367; 514/375; 514/395; 548/159; 548/163; 548/220; 548/221; 548/222; 548/307.4

(58) Field of Classification Search ................ None
See application file for complete search history.

(56) References Cited

U.S. PATENT DOCUMENTS

| 4,046,553 A | 9/1977 | Takahashi et al. |
| 5,199,970 A | 4/1993 | Tompa et al. |

FOREIGN PATENT DOCUMENTS

| JP | 02017187 | * | 1/1990 |
| WO | 03/037085 A1 | | 5/2003 |
| WO | WO 03/037085 | * | 5/2003 |

OTHER PUBLICATIONS

English machine translation of JP 02-017187. Obtained from <http://www.ipdl.inpit.go.jp/homepg_e.ipdl> Sep. 15, 2011.*

* cited by examiner

*Primary Examiner* — Joseph K. McKane
*Assistant Examiner* — Alicia L Otton
(74) *Attorney, Agent, or Firm* — Sughrue Mion, PLLC

(57) ABSTRACT

The present invention relates to an optically active (R)-aryloxypropionic acid amide compound which has high selectivity and safety for protecting a crop such as rice, wheat, barley and soy bean, and exhibits excellent herbicidal activity against weeds, and a herbicidal composition comprising the same.

9 Claims, No Drawings

OPTICALLY ACTIVE (R)-ARYLOXYPROPIONIC ACID AMIDES AND HERBICIDAL COMPOSITION COMPRISING SAME

CROSS REFERENCE TO RELATED APPLICATION

This application is a National Stage of International Application No. PCT/KR2008/003899, filed Jul. 2, 2008, claiming priority based on Korean Patent Application No. 10-2007-0066270, filed Jul. 3, 2007, the contents of all of which are incorporated herein by reference in their entirety.

FIELD OF THE INVENTION

The present invention relates to an optically active (R)-aryloxypropionic acid compound and a herbicidal composition comprising the same.

BACKGROUND OF THE INVENTION

There have been reported numerous compounds having herbicidal activity for weed control.

For example, U.S. Pat. No. 4,130,413 discloses a compound of formula (II):

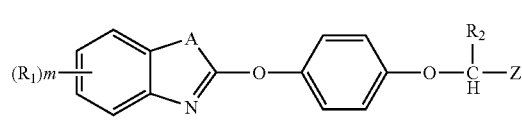

(II)

wherein, A is O, S or NH; $R_1$ is hydrogen, halogen, $CF_3$, $NO_2$, CN or alkyl; $R_2$ is hydrogen or alkyl; Z is —CON—$R_9R_{10}$, $R_9$ and $R_{10}$ being each independently $C_{1-6}$ alkyl, $C_{1-6}$ hydroxyalkyl, $C_{3-6}$ cycloalkyl, $C_{1-4}$ alkoxy or phenyl, substituted with 1 to 3 substituents selected from the group consisting of hydrogen, $C_{1-4}$ alkyl, $C_{1-6}$ alkoxy, halogen and $CF_3$; and m is 0, 1 or 2.

U.S. Pat. No. 4,531,969 discloses a compound of formula (III):

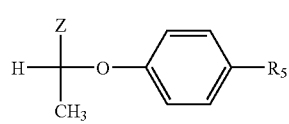

(III)

wherein, $R_5$ is

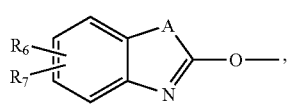

$R_6$ being hydrogen or halogen, $R_7$ being hydrogen or alkyl; Z is —CON—$R_9R_{10}$, $R_9$ and $R_{10}$ being each independently $C_{1-6}$ alkyl, $C_{1-6}$ hydroxyalkyl, $C_{3-6}$ cycloalkyl, $C_{1-4}$ alkoxy or phenyl, substituted with 1 to 3 substituents selected from the group consisting of hydrogen, $C_{1-4}$ alkyl, $C_{1-6}$ alkoxy, halogen and $CF_3$.

U.S. Pat. No. 5,254,527 discloses a compound of formula (IV):

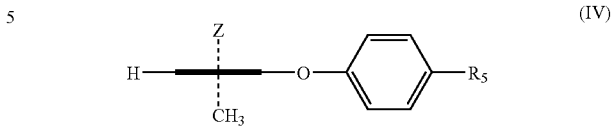

(IV)

wherein, $R_5$ and Z have the same meanings as defined above.

Japanese Laid-open Patent Publication No. Hei 2-11580 discloses a compound of formula (V).

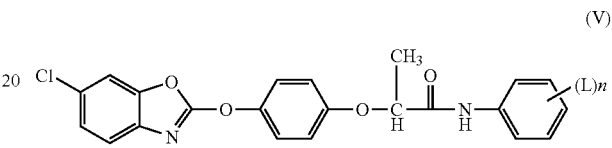

(V)

wherein, L is low alkyl, halogen, methoxy, methoxyphenoxy, benzyloxy, methylthio or methylvinyl; n is 0 or 2.

The above-mentioned compounds are satisfactory in terms of selectivity and safety for desired crop plants, but not completely satisfactory for the weed control.

SUMMARY OF THE INVENTION

Accordingly, it is a primary object of the present invention to provide a novel compound, which has high selectivity and safety for protecting of crop plants such as rice, wheat, barley and soy bean, and exhibits excellent herbicidal activity against weeds, and a method for the preparation of said compound.

It is another object of the present invention to provide a herbicidal composition comprising said compound as an active ingredient.

In accordance with one aspect of the present invention, there is provided an optically active (R)-aryloxypropionic acid amide compound of formula (I):

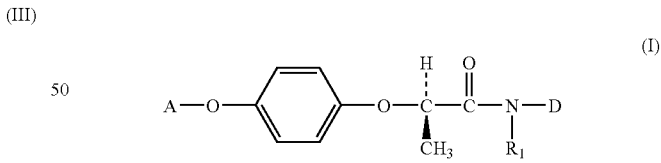

(I)

wherein,

A is fluorophenylvinyl, cyanofluorophenyl or chlorobenzoxazolyl, optionally substituted with one or more substituents each independently selected from the group consisting of $CF_3$, halogen and $C_{1-4}$ alkyl;

D is fluorophenyl, benzoxazolyl, benzothiazolyl, benzimidazolyl, pyrazolyl, pyridinyl, pyrazinyl or thiazolyl, optionally substituted with one or more substituents each independently selected from the group consisting of halogen, $C_{1-4}$ alkyl and $C_{1-4}$ alkoxy, with the proviso that when A is chlorobenzoxazolyl, D is not fluorophenyl; and $R_1$ is hydrogen or $C_{1-4}$ alkyl.

DETAILED DESCRIPTION OF THE INVENTION

Among the compounds of formula (I) of the present invention, preferred are those wherein:

A is 1-fluoro-2-phenylvinyl, 1-fluoro-2-(4-fluorophenyl) vinyl, 1,3,3,3-tetrafluoro-2-phenylpropen-1-yl, 1,3,3,3-tetrafluoro-2-(4-fluorophenyl)propen-1-yl, 1-fluoro-2-(4-methylphenyl)vinyl, 1-fluoro-2-(4-chlorophenyl)vinyl, 1,3,3,3-tetrafluoro-2-(4-chlorophenyl)propen-1-yl, 6-chlorobenzoxazolyl or 4-cyano-2-fluorophenyl;

D is 2-fluorophenyl, 5-chloro-2-benzoxazolyl, 1-methyl-2-benzimidazolyl, 2-benzthiazolyl, 6-chloro-2-benzthiazolyl, 6-fluoro-2-benzthiazolyl, 6-methyl-2-benzthiazolyl, 6-methoxy-2-benzthiazolyl, 5-chloro-2-benzoxazolyl, 1,3-dimethyl-5-pyrazolyl, 2-thiazolyl, 4-methyl-2-pyridinyl, 2-pyrazinyl or 5-chloro-2-pyridinyl, with the proviso that when A is chlorobenzoxazolyl, D is not fluorophenyl; and $R_1$ is hydrogen or methyl.

More preferred compounds of formula (I) according to the present invention are:

(1) (R)-2-[4-(6-chloro-2-benzoxazolyloxy)phenoxy]propionic acid-N-(5-chloro-2-benzoxazolyl)amide;
(2) (R)-2-[4-(6-chloro-2-benzoxazolyloxy)phenoxy]propionic acid-N-(5-chloro-2-benzoxazolyl)-N-methyl amide;
(3) (R)-2-[4-(6-chloro-2-benzoxazolyloxy)phenoxy]propionic acid-N-(1-methyl-2-benzimidazolyl)amide;
(4) (R)-2-[4-(6-chloro-2-benzoxazolyloxy)phenoxy]propionic acid-N-(1-methyl-2-benzimidazolyl)-N-methyl amide;
(5) (R)-2-[4-(6-chloro-2-benzoxazolyloxy)phenoxy]propionic acid-N-(2-benzothiazolyl)amide;
(6) (R)-2-[4-(6-chloro-2-benzoxazolyloxy)phenoxy]propionic acid-N-(2-benzothiazolyl)-N-methyl amide;
(7) (R)-2-[4-(6-chloro-2-benzoxazolyloxy)phenoxy]propionic acid-N-(6-chloro-2-benzothiazolyl)amide;
(8) (R)-2-[4-(6-chloro-2-benzoxazolyloxy)phenoxy]propionic acid-N-(6-chloro-2-benzothiazolyl)-N-methyl amide;
(9) (R)-2-[4-(6-chloro-2-benzoxazolyloxy)phenoxy]propionic acid-N-(6-fluoro-2-benzothiazolyl)amide;
(10) (R)-2-[4-(6-chloro-2-benzoxazolyloxy)phenoxy]propionic acid-N-(6-fluoro-2-benzothiazolyl)-N-methyl amide;
(11) (R)-2-[4-(6-chloro-2-benzoxazolyloxy)phenoxy]propionic acid-N-(6-methyl-2-benzothiazolyl)amide;
(12) (R)-2-[4-(6-chloro-2-benzoxazolyloxy)phenoxy]propionic acid-N-(6-methyl-2-benzothiazolyl)-N-methyl amide;
(13) (R)-2-[4-(6-chloro-2-benzoxazolyloxy)phenoxy]propionic acid-N-(6-methoxy-2-benzothiazolyl)amide;
(14) (R)-2-[4-(6-chloro-2-benzoxazolyloxy)phenoxy]propionic acid-N-(6-methoxy-2-benzothiazolyl)-N-methyl amide;
(15) (R)-2-[4-(4-cyano-2-fluorophenoxy)phenoxy]propionic acid-N-(5-chloro-2-benzoxazolyl)amide;
(16) (R)-2-[4-(4-cyano-2-fluorophenoxy)phenoxy]propionic acid-N-(5-chloro-2-benzoxazolyl)-N-methyl amide;
(17) (R)-2-[4-(4-cyano-2-fluorophenoxy)phenoxy]propionic acid-N-(1-methyl-2-benzimidazolyl)amide;
(18) (R)-2-[4-(4-cyano-2-fluorophenoxy)phenoxy]propionic acid-N-(1-methyl-2-benzimidazolyl)-N-methyl amide;
(19) (R)-2-[4-(4-cyano-2-fluorophenoxy)phenoxy]propionic acid-N-(2-benzothiazolyl)amide;
(20) (R)-2-[4-(4-cyano-2-fluorophenoxy)phenoxy]propionic acid-N-(2-benzothiazolyl)-N-methyl amide;
(21) (R)-2-[4-(4-cyano-2-fluorophenoxy)phenoxy]propionic acid-N-(6-chloro-2-benzothiazolyl)amide;
(22) (R)-2-[4-(4-cyano-2-fluorophenoxy)phenoxy]propionic acid-N-(6-chloro-2-benzothiazolyl)-N-methyl amide;
(23) (R)-2-[4-(4-cyano-2-fluorophenoxy)phenoxy]propionic acid-N-(6-fluoro-2-benzothiazolyl)amide;
(24) (R)-2-[4-(4-cyano-2-fluorophenoxy)phenoxy]propionic acid-N-(6-fluoro-2-benzothiazolyl)-N-methyl amide;
(25) (R)-2-[4-(4-cyano-2-fluorophenoxy)phenoxy]propionic acid-N-(6-methyl-2-benzothiazolyl)amide;
(26) (R)-2-[4-(4-cyano-2-fluorophenoxy)phenoxy]propionic acid-N-(6-methyl-2-benzothiazolyl)-N-methyl amide;
(27) (R)-2-[4-(4-cyano-2-fluorophenoxy)phenoxy]propionic acid-N-(6-methoxy-2-benzothiazolyl)amide;
(28) (R)-2-[4-(4-cyano-2-fluorophenoxy)phenoxy]propionic acid-N-(6-methoxy-2-benzothiazolyl)-N-methyl amide;
(29) (R)-2-[4-(4-cyano-2-fluorophenoxy)phenoxy]propionic acid-N-(1,3-dimethyl-5-pyrazolyl)amide;
(30) (R)-2-[4-(4-cyano-2-fluorophenoxy)phenoxy]propionic acid-N-(1,3-dimethyl-5-pyrazolyl)-N-methyl amide;
(31) (R)-2-[4-(4-cyano-2-fluorophenoxy)phenoxy]propionic acid-N-(2-thiazolyl)amide;
(32) (R)-2-[4-(4-cyano-2-fluorophenoxy)phenoxy]propionic acid-N-(2-thiazolyl)-N-methyl amide;
(33) (R)-2-[4-(4-cyano-2-fluorophenoxy)phenoxy]propionic acid-N-(4-methyl-2-pyridinyl)amide;
(34) (R)-2-[4-(4-cyano-2-fluorophenoxy)phenoxy]propionic acid-N-(4-methyl-2-pyridinyl)-N-methyl amide;
(35) (R)-2-[4-(4-cyano-2-fluorophenoxy)phenoxy]propionic acid-N-(2-pyrazinyl)amide;
(36) (R)-2-[4-(4-cyano-2-fluorophenoxy)phenoxy]propionic acid-N-(2-pyrazinyl)-N-methyl amide;
(37) (R)-2-[4-(1-fluoro-2-phenylvinyloxy)phenoxy]propionic acid-N-(2-fluorophenyl)-N-methyl amide;
(38) (R)-2-[4-(1-fluoro-2-phenylvinyloxy)phenoxy]propionic acid-N-(2-fluorophenyl)amide;
(39) (R)-2-[4-(1-fluoro-2-(4-fluorophenyl)vinyloxy)phenoxy]propionic acid-N-(2-fluorophenyl)amide;
(40) (R)-2-[4-(1,3,3,3-tetrafluoro-2-(4-fluorophenyl)prop-1-enyl)phenoxy]propionic acid-N-(2-fluorophenyl)amide;
(41) (R)-2-[4-(1-fluoro-2-(4-methylphenyl)vinyloxy)phenoxy]propionic acid-N-(2-fluorophenyl)amide;
(42) (R)-2-[4-(1,3,3,3-tetrafluoro-2-phenylprop-1-enyl)phenoxy]propionic acid-N-(2-fluorophenyl)amide;
(43) (R)-2-[4-(1-fluoro-2-(4-chlorophenyl)vinyloxy)phenoxy]propionic acid-N-(2-fluorophenyl)amide;
(44) (R)-2-[4-(1,3,3,3-tetrafluoro-2-(4-chlorophenyl)prop-1-enyl)phenoxy]propionic acid-N-(2-fluorophenyl)-N-methyl amide;
(45) (R)-2-[4-(1-fluoro-2-(4-fluorophenyl)vinyloxy)phenoxy]propionic acid-N-(2-fluorophenyl)-N-methyl amide;
(46) (R)-2-[4-(1,3,3,3-tetrafluoro-2-(4-fluorophenyl)prop-1-enyl)phenoxy]propionic acid-N-(2-fluorophenyl)-N-methyl amide;
(47) (R)-2-[4-(1-fluoro-2-(4-methylphenyl)vinyloxy)phenoxy]propionic acid-N-(2-fluorophenyl)-N-methyl amide;
(48) (R)-2-[4-(1,3,3,3-tetrafluoro-2-phenylprop-1-enyl)phenoxy]propionic acid-N-(2-fluorophenyl)-N-methyl amide;
(49) (R)-2-[4-(1-fluoro-2-(4-chlorophenyl)vinyloxy)phenoxy]propionic acid-N-(2-fluorophenyl)-N-methyl amide;
(50) (R)-2-[4-(1,3,3,3-tetrafluoro-2-(4-chlorophenyl)prop-1-enyl)phenoxy]propionic acid-N-(2-fluorophenyl)-N-methyl amide;
(51) (R)-2-[4-(1-fluoro-2-phenylvinyloxy)phenoxy]propionic acid-N-(5-chloro-2-benzoxazolyl)amide;
(52) (R)-2-[4-(1-fluoro-2-(4-fluorophenyl)vinyloxy)phenoxy]propionic acid-N-(5-chloro-2-benzoxazolyl)amide;

(53) (R)-2-[4-(1,3,3,3-tetrafluoro-2-(4-fluorophenyl)prop-1-enyl)phenoxy]propionic acid-N-(5-chloro-2-benzoxazolyl)amide;
(54) (R)-2-[4-(1-fluoro-2-(4-methylphenyl)vinyloxy)phenoxy]propionic acid-N-(5-chloro-2-benzoxazolyl)amide;
(55) (R)-2-[4-(1,3,3,3-tetrafluoro-2-phenylprop-1-enyl)phenoxy]propionic acid-N-(5-chloro-2-benzoxazolyl)amide;
(56) (R)-2-[4-(1-fluoro-2-(4-chlorophenyl)vinyloxy)phenoxy]propionic acid-N-(5-chloro-2-benzoxazolyl)amide;
(57) (R)-2-[4-(1,3,3,3-tetrafluoro-2-(4-chlorophenyl)prop-1-enyl)phenoxy]propionic acid-N-(5-chloro-2-benzoxazolyl)amide;
(58) (R)-2-[4-(1-fluoro-2-phenylvinyloxy)phenoxy]propionic acid-N-(5-chloro-2-benzoxazolyl)-N-methyl amide;
(59) (R)-2-[4-(1-fluoro-2-(4-fluorophenyl)vinyloxy)phenoxy]propionic acid-N-(5-chloro-2-benzoxazolyl)-N-methyl amide;
(60) (R)-2-[4-(1,3,3,3-tetrafluoro-2-(4-fluorophenyl)prop-1-enyl)phenoxy]propionic acid-N-(5-chloro-2-benzoxazolyl)-N-methyl amide;
(61) (R)-2-[4-(1-fluoro-2-(4-methylphenyl)vinyloxy)phenoxy]propionic acid-N-(5-chloro-2-benzoxazolyl)-N-methyl amide;
(62) (R)-2-[4-(1,3,3,3-tetrafluoro-2-phenylprop-1-enyl)phenoxy]propionic acid-N-(5-chloro-2-benzoxazolyl)-N-methyl amide;
(63) (R)-2-[4-(1-fluoro-2-(4-chlorophenyl)vinyloxy)phenoxy]propionic acid-N-(5-chloro-2-benzoxazolyl)-N-methyl amide; and
(64) (R)-2-[4-(1,3,3,3-tetrafluoro-2-(4-chlorophenyl)prop-1-enyl)phenoxy]propionic acid-N-(5-chloro-2-benzoxazolyl)-N-methyl amide.

The inventive compound of formula (I) may be prepared by subjecting a compound of formula (VI) to a reaction with a compound of formula (VII) in accordance with a conventional method:

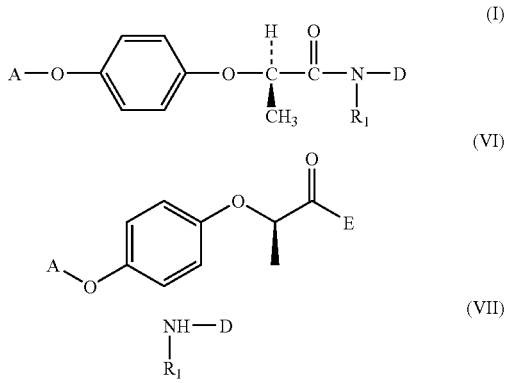

wherein,
A, D and $R_1$ have the same meanings as defined above; and
E is OH, Cl, Br or phenoxy.

The compounds of formula (VI) and formula (VII) are commercially available, or they may be prepared by conventional methods. In the above reaction, the compound of formula (VI) and the compound of formula (VII) may be employed in a mole ratio ranging from 1:1 to 3, preferably ranging from 1:1 to 1.2. This reaction may be carried out at a temperature ranging from −10° C. to 100° C. in the presence of an organic base such as triethylamine and pyridine. In this reaction, the organic base may be preferably diluted with a solvent such as ethylacetate, acetonitrile, toluene, xylene, hexane, cyclohexane, methylene chloride, dichloroethane and tetrahydrofurane. After completion of the reaction, the solvent is removed from the reaction mixture and the resulting residue is subjected to column chromatography to obtain the inventive compound of formula (I).

Alternatively, the compound of formula (I) may be obtained by subjecting a compound of formula (VIII) to a reaction with a compound of formula (IX):

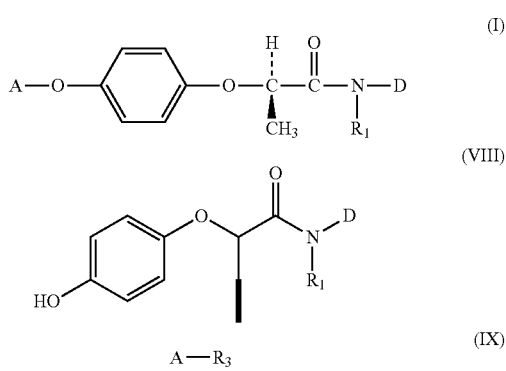

wherein,
A, D and $R_1$ have the same meanings as defined above; and
$R_3$ is hydrogen, halogen or $C_{1-4}$ alkyl.

The compounds of formula (VIII) and formula (IX) are commercially available, or they may be prepared by a conventional method. In the above reaction, the compound of formula (VIII) and the compound of formula (IX) may be employed in a mole ratio ranging from 1:1 to 3, preferably ranging from 1:1 to 1.2. This reaction may be carried out at a temperature ranging from 20° C. to 150° C. in the presence of an organic base such as triethyl amine and pyridine, or an inorganic base such as sodium hydroxide, potassium carbonate and sodium carbonate. In this reaction, the organic or inorganic base may be preferably diluted with a solvent such as ethylacetate, acetonitrile, toluene, xylene, hexane, cyclohexane, methylene chloride, dichloroethane and tetrahydrofurane. After completion of the reaction, the solvent is removed from the reaction mixture and the resulting residue is subjected to column chromatography to obtain the inventive compound of formula (I).

In accordance with further aspect of the present invention, the present invention provides a herbicidal composition comprising the compound of formula (I) as an active ingredient.

The inventive herbicidal composition may be formulated in various forms such as a wettable powder, an emulsion, granules, water-dispersible granules, a microemulsion, a suspension and a liquid, which may be prepared by mixing the compound of formula (I) with conventional additives used in the agricultural formulation. Representative examples of the additives include polyoxyethylene alkyl sulfate, polyoxyethylene alkyl phenyl sulfate, alkyl aryl sulfonate, alkenyl sulfonate, higher fatty acid, alkyl taurinate, dialkyl sulphosuccinate, polyoxyethylene alkyl ether, xanthan gum, polyoxyethylene alkylphenyl ether, polyoxyethylene styrylphenyl ether and a mixture thereof. Such formulations may be diluted using conventional diluents, if necessary. Representative examples of the diluents used in the present invention include clay minerals such as agalmatolite, talc, kaoline, clay, calcium carbonate, bentonite, silicic acid, silica powder, diatomite, gypsum, pumice and a mixture thereof. Representative examples of the solvent used in the present invention include xylene, cyclohexanone, methylnaphthalene, N-methyl-2-pyrrolidone, water and a mixture thereof.

The formulations comprise the active ingredient in an amount ranging from 0.1 to 99% by weight. The preferred amounts of each of the component contained in the formulations according to the formulation forms are shown in Table 1.

TABLE 1

| Formulation forms | % by weight | | |
|---|---|---|---|
| | Active ingredient (Compound of formula (I)) | Diluents | Additives |
| Wettable powder | 1~90 | 1~98 | 1~15 |
| Water-dispersible granules | 1~50 | 20~98 | 1~30 |
| Suspension | 1~80 | 1~95 | 1~20 |
| Emulsion or Liquid | 1~80 | 1~95 | 1~20 |
| Microemulsion | 1~50 | 20~95 | 1~30 |
| Granules | 0.01~50 | 20~98.9 | 1~30 |

The formulation may further comprise trace amounts of conventional additives for preventing the formation of foam, caking, corrosion and the microbial growth.

In accordance with the present invention, a liquid, an emulsion or a microemulsion may be readily obtained by mixing the active ingredient with the additives; a wettable powder may be obtained by grinding the mixture using a hammer mill or air mill; and water-dispersible granules may be obtained by mixing the wettable powder together with additives and extruding the mixture. Further, a suspension may be obtained by grinding the mixture using a wet mill; and granules may be obtained by mixing or extruding the active ingredients with a solid diluent, or spraying the active ingredient on a carrier.

A proposed dosage of the inventive compound used as an active ingredient in the herbicide is about from 10 g/ha to 1 kg/ha, more preferably about from 50 g/ha to 400 g/ha. It should be understood that the dosage should be determined in light of various relevant factors including the amount of weed occurrence, the stage of plant development and the form of formulation, and, therefore, the dosage suggested above should not be construed to limit the scope of the invention in anyway.

The inventive herbicide can be combined with other herbicides, insecticides and fungicides. In addition, the inventive herbicide may be combined with bensulfuronmethyl, pyrazosulfuronethyl, imazosulfuronmethyl, halosulfuronmethyl, azimsulfuron, bentazone, quinclorac, propanyl, 2,4-D, linuron, MCPA(2-methyl-4-chlorophenoxy acetic acid), azafenidine, carfentrazone, molinate, mefenacet, thiobencarb, pretilachlor, trifluralin, brooxynyl, butachlor, mecoprop, metribuzin, bifenox, cyhalofopbutyl, fentrazamide, pyriminobac methyl, bispyribac sodium, cyclosulfamuron and a mixture thereof.

The following Examples are intended to further illustrate the present invention without limiting its scope.

Example 1

Preparation of (R)-2-[4-(6-chloro-2-benzoxazolyloxy)phenoxy]propionic acid-N-(5-chloro-2-benzoxazolyl)amide (1-1): (R)-2-(4-hydroxyphenoxy)propionic acid-N-(5-chloro-2-benzoxazolyl)amide 4.0 g (0.022 mol) of (R)-2-(4-hydroxyphenoxy)propionic acid was dissolved in 25 ml of thionyl chloride, the mixture was refluxed for 5 hours, and distilled under a reduced pressure. 3.3 g (0.016 mol) of (R)-2-(4-hydroxyphenoxy)propionic acid chloride thus obtained was dissolved in 60 ml of tetrahydrofuran, and the mixture was cooled to 0° C. 3.04 g (0.018 mol) of 2-amino-5-chlorobenzoxazole and triethylamine dissolved in 15 ml of tetrahydrofuran were sequentially added to the reaction mixture. The mixture was stirred at room temperature for 5 hours, and the solvent was removed therefrom under a reduced pressure. After adding water thereto, the mixture was extracted three times with ethyl acetate three times. The combined organic layer was dried over anhydrous magnesium sulfate, filtered and distilled under a reduced pressure. The resulting residue was subjected to column chromatography (ethyl acetate:n-hexane=1:4) to obtain the title compound (4.04 g, 75.9%).

$^1$H-NMR(CDCl$_3$): δ1.6 (3H, d), 4.68 (1H, q), 6.6~6.7 (4H, m), 7.1~7.2 (3H, m), 8.13 (1H, s)

(1-2): (R)-2-[4-(6-chloro-2-benzoxazolyloxy)phenoxy]propionic acid-N-(5-chloro-2-benzoxazolyl)amide A mixture of 1.6 g (4.8 mmol) of the compound obtained in (1-1), 1.10 g (5.7 mmol) of 2,6-dichlorobenzoxazole, and 0.72 g (5.7 mmol) of potassium carbonate was added in 80 ml of acetonitrile, and the mixture was refluxed for 7 hours. The resulting mixture was cooled to room temperature and filtered to remove unreacted solid therefrom, and the filtrate was distilled under a reduced pressure. The resulting residue was subjected to column chromatography (ethyl acetate:n-hexane=1:4) to obtain the title compound (1.88 g, 80.9%).

$^1$H-NMR(CDCl$_3$): δ1.70 (3H, d), 4.91 (1H, q), 7.02~7.60 (10H, m), 9.19 (1H, s)

Example 2

Preparation of (R)-2-[4-(6-chloro-2-benzoxazolyloxy)phenoxy]propionic acid-N-(5-chloro-2-benzoxazolyl)-N-methyl amide 0.48 g (1 mmol) of the compound obtained in Example (1-2) was dissolved in anhydrous tetrahydrofuran, and the mixture was cooled to 0° C. 40 mg (1 mmol) of 60% NaH and 0.14 g (1 mmol) of methyliodide were sequentially added to the reaction mixture and the mixture was stirred at room temperature for 5 hours. Ice was added to the reaction mixture and resulting mixture was extracted three times with ethyl acetate. The organic layer was dried over anhydrous magnesium sulfate, filtered and distilled under a reduced pressure. The resulting residue was subjected to column chromatography (ethyl acetate:n-hexane=1:2) to obtain the title compound (345 mg, 71.9%).

$^1$H-NMR(CDCl$_3$): δ1.70 (3H, d), 3.84 (3H, s), 4.91 (1H, q), 7.02~7.60 (10H, m)

Example 3

Preparation of (R)-2-[4-(6-chloro-2-benzoxazolyloxy)phenoxy]propionic acid-N-(1-methyl-2-benzimidazolyl)amide (3-1): (R)-2-(4-hydroxyphenoxy)propionic acid-N-(1-methyl-2-benzimidazolyl)amide The procedure of Example (1-1) was repeated except for using 2-amino-1-methylbenzimidazole (2.65 g, 0.018 mol) instead of 2-amino-5-chlorobenzoxazole to obtain the title compound (3.98 g, 71%).

$^1$H-NMR(CDCl$_3$): δ1.7 (3H, d), 3.65 (3H, s), 4.68 (1H, q), 6.9~7.1 (4H, m), 7.25~7.41 (4H, m), 12.03 (1H, s)

(3-2): (R)-2-[4-(6-chloro-2-benzoxazolyloxy)phenoxy]propionic acid-N-(1-methyl-2-benzimidazolyl) amide The procedure of Example (1-2) was repeated except for using (R)-2-(4-hydroxyphenoxy)propionic acid-N-(1-methyl-2-benzimidazolyl)amide (1.5 g, 4.8 mmol) obtained in (3-1) instead of (R)-2-(4-hydroxyphenoxy)propionic acid-N-(6-chloro-2-benzoxazolyl)amide to obtain the title compound (1.83 g, 82.4%). $^1$H-NMR(CDCl$_3$): δ1.7 (3H, d), 3.65 (3H, s), 4.68 (1H, q), 7.02~7.41 (11H, m), 12.01 (1H, s)

Example 4

Preparation of (R)-2-[4-(6-chloro-2-benzoxazolyloxy)phenoxy]propionic acid-N-(1-methyl-2-benzimidazolyl)-N-methyl amide The procedure of Example 2 was repeated except for using (R)-2-[4-(6-chloro-2-benzoxazolyloxy)phenoxy]propionic acid-N-(1-methyl-2-benzimidazolyl)amide (0.46 g, 1 mmol) obtained in Example (3-2) instead of (R)-2-[4-(6-chloro-2-benzoxazolyloxy)phenoxy]propionic acid-N-(5-chloro-2-benzoxazolyl)amide to obtain the title compound (305 mg, 64.5%).
$^1$H-NMR(CDCl$_3$): δ1.70 (3H, d), 3.65 (3H, s), 3.84 (3H, s), 4.91 (1H, q), 7.02~7.41 (10H, m)

Example 5

Preparation of (R)-2-[4-(6-chloro-2-benzoxazolyloxy)phenoxy]propionic acid-N-(2-benzothiazolyl) amide (5-1): (R)-2-(4-hydroxyphenoxy)propionic acid-N-(2-benzothiazolyl)amide The procedure of Example (1-1) was repeated except for using 2-aminobenzothiazole (2.72 g, 0.018 mol) instead of 2-amino-5-chlorobenzoxazole to obtain the title compound (4.61 g, 81.5%).
$^1$H-NMR(CDCl$_3$): δ1.7 (3H, d), 4.68 (1H, q), 6.6~6.7 (4H, m), 7.1~7.2 (3H, m), 8.13 (1H, s)

(5-2): (R)-2-[4-(6-chloro-2-benzoxazolyloxy)phenoxy]propionic acid-N-(2-benzothiazolyl)amide The procedure of Example (1-2) was repeated except for using (R)-2-(4-hydroxyphenoxy)propionic acid-N-(2-benzothiazolyl)amide (1.5 g, 4.8 mmol) obtained in (5-1) instead of (R)-2-(4-hydroxyphenoxy)propionic acid-N-(6-chloro-2-benzoxazolyl)amide to obtain the title compound (1.84 g, 82.3%).
$^1$H-NMR(CDCl$_3$): δ1.73 (3H, d), 4.96 (1H, q), 7.03~7.88 (10H, m), 9.83 (1H, s)

Example 6

Preparation of (R)-2-[4-(6-chloro-2-benzoxazolyloxy)phenoxy]propionic acid-N-(2-benzothiazolyl)-N-methyl amide The procedure of Example 2 was repeated except for using (R)-2-[4-(6-chloro-2-benzoxazolyloxy)phenoxy]propionic acid-N-(2-benzothiazolyl)amide (0.47 g, 1 mmol) obtained in Example (5-2) instead of (R)-2-[4-(6-chloro-2-benzoxazolyloxy)phenoxy]propionic acid-N-(5-chloro-2-benzoxazolyl) amide to obtain the title compound (355 mg, 74%).
$^1$H-NMR(CDCl$_3$): δ1.73 (3H, d), 3.65 (3H, s), 4.91 (1H, q), 7.02~7.88 (10H, m)

Example 7

Preparation of (R)-2-[4-(6-chloro-2-benzoxazolyloxy)phenoxy]propionic acid-N-(6-chloro-2-benzothiazolyl)amide (7-1): (R)-2-(4-hydroxyphenoxy)propionic acid-N-(6-chloro-2-benzothiazolyl) amide The procedure of Example (1-1) was repeated except for using (2-amino-6-chlorobenzothiazole (3.3 g, 0.018 mol) instead of 2-amino-5-chlorobenzoxazole to obtain the title compound (4.15 g, 66.1%).
$^1$H-NMR(CDCl$_3$): δ1.7 (3H, d), 4.68 (1H, q), 6.6~6.8 (4H, m), 7.56~8.14 (3H, m), 9.68 (1H, s)

(7-2): (R)-2-[4-(6-chloro-2-benzoxazolyloxy)phenoxy]propionic acid-N-(6-chloro-2-benzothiazolyl) amide The procedure of Example (1-2) was repeated except for using (R)-2-(4-hydroxyphenoxy)propionic acid-N-(6-chloro-2-benzothiazolyl)amide (1.67 g, 4.8 mmol) obtained in (7-1) instead of (R)-2-(4-hydroxyphenoxy)propionic acid-N-(6-chloro-2-benzoxazolyl)amide to obtain the title compound (1.64 g, 68.3%).
$^1$H-NMR(CDCl$_3$): δ1.68 (3H, d), 4.91 (1H, q), 6.73~7.79 (10H, m), 9.70 (1H, s)

Example 8

Preparation of (R)-2-[4-(6-chloro-2-benzoxazolyloxy)phenoxy]propionic acid-N-(6-chloro-2-benzothiazolyl)-N-methyl amide The procedure of Example 2 was repeated except for using (R)-2-[4-(6-chloro-2-benzoxazolyloxy)phenoxy]propionic acid-N-(6-chloro-2-benzothiazolyl)amide (0.5 g, 1 mmol) obtained in Example (7-2) instead of (R)-2-[4-(6-chloro-2-benzoxazolyloxy)phenoxy]propionic acid-N-(5-chloro-2-benzoxazolyl)amide to obtain the title compound (360 mg, 70%).
$^1$H-NMR(CDCl$_3$): δ1.68 (3H, d), 3.64 (3H, s), 4.91 (1H, q), 6.92~7.78 (10H, m)

Example 9

Preparation of (R)-2-[4-(6-chloro-2-benzoxazolyloxy)phenoxy]propionic acid-N-(6-fluoro-2-benzothiazolyl)amide (9-1): (R)-2-(4-hydroxyphenoxy)propionic acid-N-(6-fluoro-2-benzothiazolyl)amide The procedure of Example (1-1) was repeated except for using 2-amino-6-fluorobenzothiazole (3.03 g, 0.018 mol) instead of 2-amino-5-chlorobenzoxazole to obtain the title compound (4.78 g, 79.9%).

$^1$H-NMR(CDCl$_3$): δ1.7 (3H, d), 4.68 (1H, q), 6.6~6.9 (4H, m), 7.26~8.2 (3H, m), 9.68 (1H, s)

(9-2): (R)-2-[4-(6-chloro-2-benzoxazolyloxy)phenoxy]propionic acid-N-(6-fluoro-2-benzothiazolyl)amide The procedure of Example (1-2) was repeated except for using (R)-2-(4-hydroxyphenoxy)propionic acid-N-(6-fluoro-2-benzothiazolyl)amide (1.60 g, 4.8 mmol) obtained in (9-1) instead of (R)-2-(4-hydroxyphenoxy)propionic acid-N-(6-chloro-2-benzoxazolyl)amide to obtain the title compound (1.93 g, 83.1%).
$^1$H-NMR(CDCl$_3$): δ1.69 (3H, d), 4.93 (1H, q), 6.73~7.74 (10H, m), 9.84 (1H, s)

Example 10

Preparation of (R)-2-[4-(6-chloro-2-benzoxazolyloxy)phenoxy]propionic acid-N-(6-fluoro-2-benzothiazolyl)-N-methyl amide The procedure of Example 2 was repeated except for using (R)-2-[4-(6-chloro-2-benzoxazolyloxy)phenoxy]propionic acid-N-(6-fluoro-2-benzothiazolyl)amide (0.49 g, 1 mmol) obtained in Example (9-2) instead of (R)-2-[4-(6-chloro-2-benzoxazolyloxy)phenoxy]propionic acid-N-(5-chloro-2-benzoxazolyl)amide to obtain the title compound (350 mg, 69.3%).
$^1$H-NMR(CDCl$_3$): δ1.68 (3H, d), 3.64 (3H, s), 4.91 (1H, q), 6.72~7.78 (10H, m)

Example 11

Preparation of (R)-2-[4-(6-chloro-2-benzoxazolyloxy)phenoxy]propionic acid-N-(6-methyl-2-benzothiazolyl)amide (11-1): (R)-2-(4-hydroxyphenoxy)propionic acid-N-(6-methyl-2-benzothiazolyl)amide The procedure of Example (1-1) was repeated except for using 2-amino-6-methylbenzothiazole (2.96 g, 0.018 mol) instead of 2-amino-5-chlorobenzoxazole to obtain the title compound (4.91 g, 83.1%).
$^1$H-NMR(CDCl$_3$): δ1.7 (3H, d), 2.44 (3H, s), 4.89 (1H, q), 6.6~6.9 (4H, m), 7.35~8.01 (3H, m), 9.71 (1H, s)

(11-2): (R)-2-[4-(6-chloro-2-benzoxazolyloxy)phenoxy]propionic acid-N-(6-methyl-2-benzothiazolyl)amide The procedure of Example (1-2) was repeated except for using (R)-2-(4-hydroxyphenoxy)propionic acid-N-(6-methyl-2-benzothiazolyl)amide (1.58 g, 4.8 mmol) obtained in (11-1) instead of (R)-2-(4-hydroxyphenoxy)propionic acid-N-(6-chloro-2-benzoxazolyl)amide to obtain the title compound (1.87 g, 81.2%).
$^1$H-NMR(CDCl$_3$): δ1.69 (3H, d), 2.44 (3H, s), 4.89 (1H, q), 6.95~7.65 (10H, m), 9.71 (1H, s)

Example 12

Preparation of (R)-2-[4-(6-chloro-2-benzoxazolyloxy)phenoxy]propionic acid-N-(6-methyl-2-benzothiazolyl)-N-methyl amide The procedure of Example 2 was repeated except for using (R)-2-[4-(6-chloro-2-benzoxazolyloxy)phenoxy]propionic acid-N-(6-methyl-2-benzothiazolyl)amide (0.48 g, 1 mmol) obtained in Example (11-2) instead of (R)-2-[4-(6-chloro-2-benzoxazolyloxy)phenoxy]propionic acid-N-(5-chloro-2-benzoxazolyl)amide to obtain the title compound (323 mg, 65.3%).
$^1$H-NMR(CDCl$_3$): δ1.68 (3H, d), 2.44 (3H, s), 3.64 (3H, s), 4.91 (1H, q), 6.72~7.78 (10H, m)

Example 13

Preparation of (R)-2-[4-(6-chloro-2-benzoxazolyloxy)phenoxy]propionic acid-N-(6-methoxy-2-benzothiazolyl)amide (13-1): (R)-2-(4-hydroxyphenoxy)propionic acid-N-(6-methoxy-2-benzothiazolyl)amide The procedure of Example (1-1) was repeated except for using 2-amino-6-methoxybenzothiazole (3.25 g, 0.018 mol) instead of 2-amino-5-chlorobenzoxazole to obtain the title compound (5.05 g, 81.5%).
$^1$H-NMR(CDCl$_3$): δ1.7 (3H, d), 3.87 (3H, s), 4.89 (1H, q), 6.6~6.9 (4H, m), 7.35~8.01 (3H, m), 9.71 (1H, s)

(13-2): (R)-2-[4-(6-chloro-2-benzoxazolyloxy)phenoxy]propionic acid-N-(6-methoxy-2-benzothiazolyl)amide The procedure of Example (1-2) was repeated except for using (R)-2-(4-hydroxyphenoxy)propionic acid-N-(6-methoxy-2-benzothiazolyl)amide (1.58 g, 4.8 mmol) obtained in (13-1) instead of (R)-2-(4-hydroxyphenoxy)propionic acid-N-(6-chloro-2-benzoxazolyl)amide to obtain the title compound (2.09 g, 87.8%).
$^1$H-NMR(CDCl$_3$): δ1.67 (3H, d), 3.87 (3H, s), 4.92 (1H, q), 7.02~7.44 (10H, m), 9.73 (1H, s)

Example 14

Preparation of (R)-2-[4-(6-chloro-2-benzoxazolyloxy)phenoxy]propionic acid-N-(6-methoxy-2-benzothiazolyl)-N-methyl amide The procedure of Example 2 was repeated except for using (R)-2-[4-(6-chloro-2-benzoxazolyloxy)phenoxy]propionic acid-N-(6-methoxy-2-benzothiazolyl)amide (0.5 g, 1 mmol) obtained in Example (13-2) instead of (R)-2-[4-(6-chloro-2-benzoxazolyloxy)phenoxy]propionic acid-N-(5-chloro-2-benzoxazolyl)amide to obtain the title compound (368 mg, 71.5%).
$^1$H-NMR(CDCl$_3$): δ1.68 (3H, d), 3.64 (3H, s), 3.87 (3H, s), 4.91 (1H, q), 6.72~7.46 (10H, m)

Example 15

Preparation of (R)-2-[4-(4-cyano-2-fluorophenoxy)phenoxy]propionic acid-N-(5-chloro-2-benzoxazolyl)amide A mixture of 1.6 g (4.8 mmol) of the compound obtained in Example (1-1), 0.8 g (5.7 mmol) of 3,4-difluorobenzonitrile and 0.72 g (5.7 mmol) of potassium carbonate was added in 100 ml of acetonitrile, and the mixture was reflexed for 7 hours. The mixture was cooled to room temperature and filtered to remove unreacted solid therefrom, and the filtrate was distilled under a reduced pressure. The resulting residue was subjected to column chromatography (ethyl acetate:n-hexane=1:4) to obtain the title compound (1.83 g, 84.4%).

$^1$H-NMR(CDCl$_3$): δ1.72 (3H, d), 4.88 (1H, q), 6.88~7.59 (10H, m), 9.32 (1H, s)

Example 16

Preparation of (R)-2-[4-(4-cyano-2-fluorophenoxy)phenoxy]propionic acid-N-(5-chloro-2-benzoxazolyl)-N-methyl amide The procedure of Example 2 was repeated except for using (R)-2-[4-(4-cyano-2-fluorophenoxy)phenoxy]propionic acid-N-(5-chloro-2-benzoxazolyl)amide (0.45 g, 1 mmol) obtained in Example 15 instead of (R)-2-[4-(6-chloro-2-benzoxazolyloxy)phenoxy]propionic acid-N-(5-chloro-2-benzoxazolyl)amide to obtain the title compound (302 mg, 65%).

$^1$H-NMR(CDCl$_3$): δ1.72 (3H, d), 3.64 (3H, s), 4.90 (1H, q), 6.88~7.56 (10H, m)

Example 17

Preparation of (R)-2-[4-(4-cyano-2-fluorophenoxy)phenoxy]propionic acid-N-(1-methyl-2-benzimidazolyl)amide The procedure of Example 15 was repeated except for using (R)-2-(4-hydroxyphenoxy)propionic acid-N-(1-methyl-2-benzimidazolyl)amide (1.5 g, 4.8 mmol) obtained in Example (3-1) instead of (R)-2-(4-hydroxyphenoxy)propionic acid-N-(5-chloro-2-benzoxazolyl)amide to obtain the title compound (1.64 g, 79.3%).

$^1$H-NMR(CDCl$_3$): δ1.68 (3H, d), 3.63 (3H, s), 4.64 (1H, q), 6.79~7.43 (11H, m) 12.01 (1H, s)

Example 18

Preparation of (R)-2-[4-(4-cyano-2-fluorophenoxy)phenoxy]propionic acid-N-(1-methyl-2-benzimidazolyl)-N-methyl amide The procedure of Example 2 was repeated except for using (R)-2-[4-(4-cyano-2-fluorophenoxy)phenoxy]propionic acid-N-(1-methyl-2-benzimidazolyl)amide (0.45 g, 1 mmol) obtained in Example 17 instead of (R)-2-[4-(6-chloro-2-benzoxazolyloxy)phenoxy]propionic acid-N-(5-chloro-2-benzoxazolyl)amide to obtain the title compound (302 mg, 65%).

$^1$H-NMR(CDCl$_3$): δ1.72 (3H, d), 3.64 (3H, s), 4.64 (1H, q), 6.80~7.46 (10H, m)

Example 19

Preparation of (R)-2-[4-(4-cyano-2-fluorophenoxy)phenoxy]propionic acid-N-(2-benzothiazolyl)amide The procedure of Example 15 was repeated except for using (R)-2-(4-hydroxyphenoxy)propionic acid-N-(2-benzothiazolyl)amide (1.5 g, 4.8 mmol) obtained in Example (5-1) instead of (R)-2-(4-hydroxyphenoxy)propionic acid-N-(5-chloro-2-benzoxazolyl)amide to obtain the title compound (1.75 g, 84.1%).

$^1$H-NMR(CDCl$_3$): δ1.68 (3H, d), 4.87 (1H, q), 6.73~7.83 (11H, m), 10.07 (1H, s)

Example 20

Preparation of (R)-2-[4-(4-cyano-2-fluorophenoxy)phenoxy]propionic acid-N-(2-benzothiazolyl)-N-methyl amide The procedure of Example 2 was repeated except for using (R)-2-[4-(4-cyano-2-fluorophenoxy)phenoxy]propionic acid-N-(2-benzothiazolyl)amide (0.44 g, 1 mmol) obtained in Example 19 instead of (R)-2-[4-(6-chloro-2-benzoxazolyloxy)phenoxy]propionic acid-N-(5-chloro-2-benzoxazolyl)amide to obtain the title compound (322 mg, 70.1%).

$^1$H-NMR(CDCl$_3$): δ1.72 (3H, d), 3.64 (3H, s), 4.87 (1H, q), 6.73~7.76 (10H, m)

Example 21

Preparation of (R)-2-[4-(4-cyano-2-fluorophenoxy)phenoxy]propionic acid-N-(6-chloro-2-benzothiazolyl)amide The procedure of Example 15 was repeated except for using (R)-2-(4-hydroxyphenoxy)propionic acid-N-(6-chloro-2-benzothiazolyl)amide (1.67 g, 4.8 mmol) obtained in Example (7-1) instead of (R)-2-(4-hydroxyphenoxy)propionic acid-N-(5-chloro-2-benzoxazolyl)amide to obtain the title compound (1.60 g, 71.2%).

$^1$H-NMR(CDCl$_3$): δ1.69 (3H, d), 4.90 (1H, q), 6.85~7.79 (10H, m), 9.76 (1H, s)

Example 22

Preparation of (R)-2-[4-(4-cyano-2-fluorophenoxy)phenoxy]propionic acid-N-(6-chloro-2-benzothiazolyl)-N-methyl amide The procedure of Example 2 was repeated except for using (R)-2-[4-(4-cyano-2-fluorophenoxy)phenoxy]propionic acid-N-(6-chloro-2-benzothiazolyl)amide (0.47 g, 1 mmol) obtained in Example 21 instead of (R)-2-[4-(6-chloro-2-benzoxazolyloxy)phenoxy]propionic acid-N-(5-chloro-2-benzoxazolyl)amide to obtain the title compound (312 mg, 64.3%).

$^1$H-NMR(CDCl$_3$): δ1.69 (3H, d), 3.65 (3H, s), 4.90 (1H, q), 6.83~7.76 (10H, m)

Example 23

Preparation of (R)-2-[4-(4-cyano-2-fluorophenoxy)phenoxy]propionic acid-N-(6-fluoro-2-benzothiazolyl)amide The procedure of Example 15 was repeated except for using (R)-2-(4-hydroxyphenoxy)propionic acid-N-(6-fluoro-2-benzothiazolyl)amide (1.60 g, 4.8 mmol) obtained in Example (9-1) instead of (R)-2-(4-hydroxyphenoxy)propionic acid-N-(5-chloro-2-benzoxazolyl)amide to obtain the title compound (1.73 g, 79.8%).

¹H-NMR(CDCl₃): δ1.72 (3H, d), 4.91 (1H, q), 6.76~7.76 (10H, m), 9.88 (1H, s)

Example 24

Preparation of (R)-2-[4-(4-cyano-2-fluorophenoxy)phenoxy]propionic acid-N-(6-fluoro-2-benzothiazolyl)-N-methyl amide The procedure of Example 2 was repeated except for using (R)-2-[4-(4-cyano-2-fluorophenoxy)phenoxy]propionic acid-N-(6-fluoro-2-benzothiazolyl)amide (0.45 g, 1 mmol) obtained in Example 23 instead of (R)-2-[4-(6-chloro-2-benzoxazolyloxy)phenoxy]propionic acid-N-(5-chloro-2-benzoxazolyl)amide to obtain the title compound (300 mg, 64.5%).

¹H-NMR(CDCl₃): δ1.69 (3H, d), 3.65 (3H, s), 4.90 (1H, q), 6.73~7.76 (10H, m)

Example 25

Preparation of (R)-2-[4-(4-cyano-2-fluorophenoxy)phenoxy]propionic acid-N-(6-methyl-2-benzothiazolyl)amide The procedure of Example 15 was repeated except for using (R)-2-(4-hydroxyphenoxy)propionic acid-N-(6-methyl-2-benzothiazolyl)amide (1.58 g, 4.8 mmol) obtained in Example (11-1) instead of (R)-2-(4-hydroxyphenoxy)propionic acid-N-(5-chloro-2-benzoxazolyl)amide to obtain the title compound (1.90 g, 88.5%).

¹H-NMR(CDCl₃): δ1.66 (3H, d), 2.44 (3H, s), 4.85 (1H, q), 6.81~7.64 (10H, m), 9.80 (1H, s)

Example 26

Preparation of (R)-2-[4-(4-cyano-2-fluorophenoxy)phenoxy]propionic acid-N-(6-methyl-2-benzothiazolyl)-N-methyl amide The procedure of Example 2 was repeated except for using (R)-2-[4-(4-cyano-2-fluorophenoxy)phenoxy]propionic acid-N-(6-methyl-2-benzothiazolyl)amide (0.45 g, 1 mmol) obtained in Example 25 instead of (R)-2-[4-(6-chloro-2-benzoxazolyloxy)phenoxy]propionic acid-N-(5-chloro-2-benzoxazolyl)amide to obtain the title compound (307 mg, 66%).

¹H-NMR(CDCl₃): δ1.69 (3H, d), 2.44 (3H, s), 3.65 (3H, s), 4.85 (1H, q), 6.81~7.66 (10H, m)

Example 27

Preparation of (R)-2-[4-(4-cyano-2-fluorophenoxy)phenoxy]propionic acid-N-(6-methoxy-2-benzothiazolyl)amide The procedure of Example 15 was repeated except for using (R)-2-(4-hydroxyphenoxy)propionic acid-N-(6-methoxy-2-benzothiazolyl)amide (1.58 g, 4.8 mmol) obtained in Example (13-1) instead of (R)-2-(4-hydroxyphenoxy)propionic acid-N-(5-chloro-2-benzoxazolyl)amide to obtain the title compound (2.05 g, 92.1%).

¹H-NMR(CDCl₃): δ1.68 (3H, d), 3.85 (3H, s), 4.87 (1H, q), 6.83~7.67 (10H, m), 9.73 (1H, s)

Example 28

Preparation of (R)-2-[4-(4-cyano-2-fluorophenoxy)phenoxy]propionic acid-N-(6-methoxy-2-benzothiazolyl)-N-methyl amide The procedure of Example 2 was repeated except for using (R)-2-[4-(4-cyano-2-fluorophenoxy)phenoxy]propionic acid-N-(6-methoxy-2-benzothiazolyl)amide (0.46 g, 1 mmol) obtained in Example 27 instead of (R)-2-[4-(6-chloro-2-benzoxazolyloxy)phenoxy]propionic acid-N-(5-chloro-2-benzoxazolyl)amide to obtain the title compound (333 mg, 70%).

¹H-NMR(CDCl₃): δ1.69 (3H, d), 3.65 (3H, s), 3.85 (3H, s), 4.85 (1H, q), 6.81~7.66 (10H, m)

Example 29

Preparation of (R)-2-[4-(4-cyano-2-fluorophenoxy)phenoxy]propionic acid-N-(1,3-dimethyl-5-pyrazolyl)amide (29-1): (R)-2-(4-hydroxyphenoxy)propionic acid-N-(1,3-dimethyl-5-pyrazolyl)amide The procedure of Example (1-1) was repeated except for using 5-amino-1,3-dimethylpyrazole (2.00 g, 0.018 mol) instead of 2-amino-5-chlorobenzoxazole to obtain the title compound (3.63 g, 73.2%).

¹H-NMR(CDCl₃): δ1.68 (3H, d), 2.25 (3H, s), 3.62 (3H, s), 4.81 (1H, q), 6.01 (1H, s), 6.60~6.84 (4H, m), 8.01 (1H, s)

(29-2): (R)-2-[4-(4-cyano-2-fluorophenoxy)phenoxy]propionic acid-N-(1,3-dimethyl-5-pyrazolyl)amide The procedure of Example 15 was repeated except for using (R)-2-(4-hydroxyphenoxy)propionic acid-N-(1,3-dimethyl-5-pyrazolyl)amide (1.32 g, 4.8 mmol) obtained in (29-1) instead of (R)-2-(4-hydroxyphenoxy)propionic acid-N-(5-chloro-2-benzoxazolyl)amide to obtain the title compound (1.65 g, 87.2%).

¹H-NMR(CDCl₃): δ1.68 (3H, d), 2.21 (3H, s), 3.59 (3H, s), 4.81 (1H, q), 6.07 (1H, s), 6.87~7.49 (7H, m), 7.98 (1H, s)

Example 30

Preparation of (R)-2-[4-(4-cyano-2-fluorophenoxy)phenoxy]propionic acid-N-(1,3-dimethyl-5-pyrazolyl)-N-methyl amide The procedure of Example 2 was repeated except for using (R)-2-[4-(4-cyano-2-fluorophenoxy)phenoxy]propionic acid-N-(1,3-dimethyl-5-pyrazolyl)amide (0.38 g, 1 mmol) obtained in Example (29-2) instead of (R)-2-[4-(6-chloro-2-benzoxazolyloxy)phenoxy]propionic acid-N-(5-chloro-2-benzoxazolyl)amide to obtain the title compound (265 mg, 67.1%).

¹H-NMR(CDCl₃): δ1.68 (3H, d), 2.21 (3H, s), 3.59 (3H, s), 3.65 (3H, s), 4.81 (1H, q), 6.07 (1H, s), 6.87~7.49 (7H, m)

Example 31

Preparation of (R)-2-[4-(4-cyano-2-fluorophenoxy)phenoxy]propionic acid-N-(2-thiazolyl)amide (31-1): (R)-2-(4-hydroxyphenoxy)propionic acid-N-(2-thiazolyl)amide The procedure of Example (1-1) was repeated except for using 2-aminothiazole (1.80 g, 0.018 mol) instead of 2-amino-5-chlorobenzoxazole to obtain the title compound (4.0 g, 84.1%).
¹H-NMR(CDCl₃): δ1.68 (3H, d), 4.86 (1H, q), 6.60~6.84 (6H, m), 10.13 (1H, s)

(31-2): (R)-2-[4-(4-cyano-2-fluorophenoxy)phenoxy]propionic acid-N-(2-thiazolyl)amide The procedure of Example 15 was repeated except for using (R)-2-(4-hydroxyphenoxy)propionic acid-N-(2-thiazolyl)amide (1.27 g, 4.8 mmol) obtained in Example (31-1) instead of (R)-2-(4-hydroxyphenoxy)propionic acid-N-(5-chloro-2-benzoxazolyl)amide to obtain the title compound (1.33 g, 72.3%).
¹H-NMR(CDCl₃): δ1.68 (3H, d), 4.86 (1H, q), 6.83~7.51 (9H, m), 10.13 (1H, s)

Example 32

(R)-2-[4-(4-cyano-2-fluorophenoxy)phenoxy]propionic acid-N-(2-thiazolyl)-N-methyl amide The procedure of Example 2 was repeated except for using (R)-2-[4-(4-cyano-2-fluorophenoxy)phenoxy]propionic acid-N-(2-thiazolyl)amide (0.38 g, 1 mmol) obtained in Example (31-2) instead of (R)-2-[4-(6-chloro-2-benzoxazolyloxy)phenoxy]propionic acid-N-(5-chloro-2-benzoxazolyl)amide to obtain the title compound (249 mg, 63%).
¹H-NMR(CDCl₃): δ1.68 (3H, d), 3.65 (3H, s), 4.86 (1H, q), 6.83~7.51 (9H, m)

Example 33

Preparation of (R)-2-[4-(4-cyano-2-fluorophenoxy)phenoxy]propionic acid-N-(4-methyl-2-pyridinyl)amide (33-1): (R)-2-(4-hydroxyphenoxy)propionic acid-N-(4-methyl-2-pyridinyl)amide The procedure of Example (1-1) was repeated except for using 2-amino-4-methylpyridine (1.95 g, 0.018 mol) instead of 2-amino-5-chlorobenzoxazole to obtain the title compound (4.1 g, 83.6%).
¹H-NMR(CDCl₃): δ1.68 (3H, d), 2.38 (2H, s), 4.76 (1H, q), 6.80-7.25 (7H, m), 8.78 (1H, s)

(33-2): (R)-2-[4-(4-cyano-2-fluorophenoxy)phenoxy]propionic acid-N-(4-methyl-2-pyridinyl)amide The procedure of Example 15 was repeated except for using (R)-2-(4-hydroxyphenoxy)propionic acid-N-(4-methyl-2-pyridinyl)amide (1.31 g, 4.8 mmol) obtained in (33-1) instead of (R)-2-(4-hydroxyphenoxy)propionic acid-N-(5-chloro-2-benzoxazolyl)amide to obtain the title compound (1.29 g, 68.7%).
¹H-NMR(CDCl₃): δ1.68 (3H, d), 2.38 (2H, s), 4.76 (1H, q), 6.83~8.15 (10H, m), 8.78 (1H, s)

Example 34

Preparation of (R)-2-[4-(4-cyano-2-fluorophenoxy)phenoxy]propionic acid-N-(4-methyl-2-pyridinyl)-N-methyl amide The procedure of Example 2 was repeated except for using (R)-2-[4-(4-cyano-2-fluorophenoxy)phenoxy]propionic acid-N-(4-methyl-2-pyridinyl)amide (0.39 g, 1 mmol) obtained in Example (33-2) instead of (R)-2-[4-(6-chloro-2-benzoxazolyloxy)phenoxy]propionic acid-N-(5-chloro-2-benzoxazolyl)amide to obtain the title compound (269 mg, 66.4%).
¹H-NMR(CDCl₃): δ1.68 (3H, d), 2.38 (2H, s), 3.65 (3H, s), 4.76 (1H, q), 6.83~8.15 (10H, m)

Example 35

Preparation of (R)-2-[4-(4-cyano-2-fluorophenoxy)phenoxy]propionic acid-N-(2-pyrazinyl)amide (35-1): (R)-2-(4-hydroxyphenoxy)propionic acid-N-(2-pyrazinyl)amide The procedure of Example (1-1) was repeated except for using 2-aminopyrazine (1.71 g, 0.018 mol) instead of 2-amino-5-chlorobenzoxazole to obtain the title compound (4.1 g, 87.9%).
¹H-NMR(CDCl₃): δ1.70 (3H, d), 4.83 (1H, q), 6.67~8.24 (7H, m), 8.80 (1H, s), 9.61 (1H, s)

(35-2): (R)-2-[4-(4-cyano-2-fluorophenoxy)phenoxy]propionic acid-N-(2-pyrazinyl)amide The procedure of Example 15 was repeated except for using (R)-2-(4-hydroxyphenoxy)propionic acid-N-(2-pyrazinyl)amide (1.25 g, 4.8 mmol) obtained in (35-1) instead of (R)-2-(4-hydroxyphenoxy)propionic acid-N-(5-chloro-2-benzoxazolyl)amide to obtain the title compound (1.34 g, 73.8%).
¹H-NMR(CDCl₃): δ1.70 (3H, d), 4.83 (1H, q), 6.87-8.40 (10H, m), 8.80 (1H, s), 9.61 (1H, s)

Example 36

Preparation of (R)-2-[4-(4-cyano-2-fluorophenoxy)phenoxy]propionic acid-N-(2-pyrazinyl)-N-methyl amide The procedure of Example 2 was repeated except for using (R)-2-[4-(4-cyano-2-fluorophenoxy)phenoxy]propionic acid-N-(2-pyrazinyl)amide (0.38 g, 1 mmol) obtained in Example (35-2) instead of (R)-2-[4-(6-chloro-2-benzoxazolyloxy)phenoxy]propionic acid-N-(5-chloro-2-benzoxazolyl)amide to obtain the title compound (239 mg, 60.5%).

$^1$H-NMR(CDCl$_3$): δ1.68 (3H, d), 3.65 (3H, s), 4.83 (1H, q), 6.83~8.40 (10H, m)

Example 37

Preparation of (R)-2-[4-(1-fluoro-2-phenylvinyloxy) phenoxy]propionic acid-N-(2-fluorophenyl)-N-methyl amide (1)

(37-1):difluorostyrene 5.25 g (0.02 mol) of triphenyl phosphine was dissolved in 20 ml of dichloromethane, and the mixture was cooled to 0° C. 2.1 g (0.01 mol) of dibromodifluoromethane was added to the mixture using an injector, and the reaction mixture was stirred for 30 minutes at room temperature. 1.06 g (0.01 mol) of benzaldehyde was added thereto and the mixture was refluxed for 4 hours. The resulting mixture was distilled under a reduced pressure at 40° C./1 mmHg using a distilling apparatus to obtain the title compound (0.81 g, 57.5%).
$^1$H-NMR(CDCl$_3$): δ5.21 (1H, s), 7.14~7.30 (5H, m)

(37-2): (S)-2-bromo-propionic acid-N-(2-fluorophenyl)amide

A mixture of 6.8 g (0.044 mol) of (S)-2-bromopropionic acid and 5.33 g (0.048 mol) of 2-fluoroanyaniline was dissolved in 100 ml of chloroform, and the mixture was cooled to 0° C. 10 g (0.048 mol) of dicyclohexylcarbodiamide dissolved in 20 ml of chloroform was added to the reaction mixture using an injector, and the mixture was stirred at room temperature for 1 hour. The reaction mixture was filtered to remove unreacted solid therefrom and washed with 30 ml of chloroform twice. The resulting residue was subjected to column chromatography (ethyl acetate:n-hexane=1:3) to obtain the title compound (10 g, 86.1%)
$^1$H-NMR(CDCl$_3$): δ1.7 (3H, d), 4.16 (1H, q), 7.13~7.48 (4H, m)

(37-3): (R)-2-(4-hydroxyphenoxy)propionic acid-N-(2-fluorophenyl)amide

A mixture of 17.2 g (0.07 mol) of the compound obtained in (37-2), 7 g (0.064 mol) of hydroquinone, 10.54 g (0.076 mol) of potassium carbonate and 1 g of tetra-n-butyl ammonium bromide was added in 300 ml of acetonitrile, and the mixture was refluxed for 6 hours. The mixture was cooled to room temperature and filtered to remove unreacted solid therefrom, and the filtrate was distilled under a reduced pressure. The resulting residue was subjected to column chromatography (ethyl acetate:n-hexane=1:2) to obtain the title compound (16 g, 90.8%).
$^1$H-NMR(CDCl$_3$): δ1.42 (3H, d), 4.56 (1H, q), 6.5~7.4 (8H, m)

(37-4): (R)-2-(4-hydroxyphenoxy)propionic acid-N-(2-fluorophenyl)-N-methylamide 5.8 g (0.02 mol) of the compound obtained in (37-3) was dissolved in anhydrous tetrahydrofuran, and the mixture was cooled to 0° C. 0.8 g (0.02 mol) of 60% NaH and 2.8 g (0.02 mol) of methyliodide were sequentially added to the reaction mixture, and the mixture was stirred at room temperature for 5 hours. Ice was added to the reaction mixture and resulting mixture was extracted three times with ethyl acetate. The organic layer was dried over anhydrous magnesium sulfate, filtered and distilled under a reduced pressure. The resulting residue was subjected to column chromatography (ethyl acetate:n-hexane=1:2) to obtain the title compound (3.91 g, 67.6%).
$^1$H-NMR(CDCl$_3$): δ1.47 (3H, t), 3.29 (3H, s), 4.63 (1H, q), 5.63 (1H, dd), 6.74~7.43 (13H, m)

(37-5): (R)-2-[4-(1-fluoro-2-phenylvinyloxy)phenoxy]propionic acid-N-(2-fluorophenyl)-N-methyl amide A mixture of 5.8 g (0.02 mol) of the compound obtained in (37-4), 1.4 g (0.02 mol) of the compound obtained in Example (20-1) and 1.2 g (0.02 mol) of potassium carbonate was added in 100 ml of acetonitrile, and the mixture was reflexed for 7 hours. The resulting mixture was cooled to room temperature and filtered to remove unreacted solid therefrom, and the filtrate was distilled under a reduced pressure. The resulting residue was subjected to column chromatography (ethyl acetate:n-hexane=1:4) to obtain the title compound (7.1 g, 86.7%)
$^1$H-NMR(CDCl$_3$): δ1.47 (3H, t), 3.29 (3H, s), 4.63 (1H, q), 5.63 (1H, dd), 6.74~7.43 (13H, m)

Example 38

Preparation of (R)-2-[4-(1-fluoro-2-phenylvinyloxy) phenoxy]propionic acid-N-(2-fluorophenyl)amide The procedure of Example (37-5) was repeated except for using (R)-2-(4-hydroxyphenoxy)propionic acid-N-(2-fluorophenyl)amide (5.5 g, 0.02 mol) obtained in Example (37-3) instead of (R)-2-(4-hydroxyphenoxy)propionic acid-N-(2-fluorophenyl)-N-methylamide to obtain the title compound (7.1 g, 89.8%).
$^1$H-NMR(CDCl$_3$): δ1.47 (3H, t), 4.62 (1H, q), 5.63 (1H, dd), 6.74~7.43 (13H, m)

Example 37

Preparation of (R)-2-[4-(1-fluoro-2-phenylvinyloxy) phenoxy]propionic acid-N-(2-fluorophenyl)-N-methyl amide (2)

0.4 g (1 mmol) of the compound obtained in Example 38 was dissolved in anhydrous tetrahydrofuran, and the mixture was cooled to 0° C. 40 mg (1 mmol) of 60% NaH and 0.14 g (1 mmol) of methyliodide were sequentially added to the reaction mixture, and the mixture was stirred at room temperature for 5 hours. Ice was added to the reaction mixture and resulting mixture was extracted three times with ethyl acetate. The organic layer was dried over anhydrous magnesium sulfate, filtered and distilled under a reduced pressure. The resulting residue was subjected to column chromatography (ethyl acetate:n-hexane=1:2) to obtain the title compound (300 mg, 73.3%).
$^1$H-NMR(CDCl$_3$): δ1.47 (3H, t), 3.29 (3H, s), 4.63 (1H, q), 5.63 (1H, dd), 6.74~7.43 (13H, m)

Examples 39 to 44

The procedure of Example (37-5) was repeated except for using each of the corresponding styrene compound instead of difluorostyrene, and (R)-2-(4-hydroxyphenoxy)propionic acid-N-(2-fluorophenyl)amide obtained in Example (37-3) instead of (R)-2-(4-hydroxyphenoxy)propionic acid-N-(2-fluorophenyl)-N-methylamide to obtain the compounds shown in Table 2.

TABLE 2

| Compounds | R¹ | R² | ¹H-NMR(CDCl$_3$) |
|---|---|---|---|
| Example 39 | H | F | δ1.47 (3H, t), 4.62 (1H, q), 5.63 (1H, dd), 6.70~7.41 (12H, m), 8.56 (1H, br) |
| Example 40 | CF$_3$ | F | δ1.46 (3H, t), 4.62 (1H, q), 6.69~7.42 (12H, m), 8.5 (1H, br) |
| Example 41 | H | CH$_3$ | δ1.50 (3H, t), 2.34 (3H, s), 4.62 (1H, q), 5.64 (1H, dd), 6.69~7.36 (12H, m), 8.56 (1H, br) |
| Example 42 | CF$_3$ | H | δ1.46 (3H, t), 4.62 (1H, q), 6.69~7.42 (13H, m), 8.59 (1H, br) |
| Example 43 | H | Cl | δ1.47 (3H, t), 4.73 (1H, q). 5.59 (1H, dd), 6.83~7.38 (12H, m), 8.56 (1H, br) |
| Example 44 | CF$_3$ | Cl | δ1.46 (3H, t), 4.72 (1H, q), 6.69~7.42 (12H, m), 8.58 (1H, br) |

Examples 45 to 50

The procedure of Example (37-5) was repeated except for using each of the corresponding styrene compound instead of difluorostyrene to obtain the compounds shown in Table 3.

TABLE 3

| Compounds | R¹ | R² | ¹H-NMR (CDCl$_3$) |
|---|---|---|---|
| Example 45 | H | F | δ1.47 (3H, t), 3.29 (3H, s), 4.62 (1H, q), 5.63 (1H, dd), 6.70~7.41 (12H, m) |
| Example 46 | CF$_3$ | F | δ1.46 (3H, t), 3.29 (3H, s), 4.62 (1H, q), 6.69~7.42 (12H, m) |
| Example 47 | H | CH$_3$ | δ1.50 (3H, t), 2.34 (3H, s), 3.29 (3H, s), 4.62 (1H, q), 5.64 (1H, dd), 6.69~7.36 (12H, m) |
| Example 48 | CF$_3$ | H | δ1.46 (3H, t), 3.29 (3H, s), 4.62 (1H, q), 6.69~7.42 (13H, m) |
| Example 49 | H | Cl | δ1.47 (3H, t), 3.27 (3H, s), 4.73 (1H, q), 5.59 (1H, dd), 6.83~7.38 (12H, m) |
| Example 50 | CF$_3$ | Cl | δ1.46 (3H, t), 3.29 (3H, s), 4.72 (1H, q), 6.69~7.42 (12H, m) |

Examples 51 to 57

The procedure of Example (1-2) was repeated except for using each of the corresponding styrene compound instead of difluorostyrene to obtain the compounds shown in Table 4.

TABLE 4

| Compounds | R¹ | R² | ¹H-NMR (CDCl$_3$) |
|---|---|---|---|
| Example 51 | H | H | δ1.68 (3H, d), 4.82 (1H, q), 5.65 (1H, d), 6.87~7.60 (12H, m), 9.35 (1H, s) |
| Example 52 | H | F | δ1.68 (3H, d), 4.85 (1H, q), 5.63 (1H, d), 6.93~7.60 (11H, m), 9.23 (1H, s) |
| Example 53 | CF$_3$ | F | δ1.68 (3H, d), 4.83 (1H, q), 6.87~7.60 (11H, m), 9.30 (1H, s) |
| Example 54 | H | CH$_3$ | δ1.68 (3H, d), 2.35 (3H, s), 4.75 (1H, q), 5.66 (1H, d), 6.87~7.38 (11H, m), 9.35 (1H, s) |
| Example 55 | CF$_3$ | H | δ1.68 (3H, d), 4.82 (1H, q), 6.87~7.60 (12H, m), 9.35 (1H, s) |
| Example 56 | H | Cl | δ1.69 (3H, d), 4.85(1H, q), 5.61 (1H, d), 6.93~7.59 (11H, m), 9.29 (1H, s) |
| Example 57 | CF$_3$ | Cl | δ1.69 (3H, d), 4.82 (1H, q), 6.87~7.60 (12H, m), 9.35 (1H, s) |

Examples 58 to 64

The procedure of Example (37-4) was repeated except for using each of the compound obtained in Examples 58 to 64 instead of (R)-2-(4-hydroxyphenoxy)propionic acid-N-(2-fluorophenyl)amide to obtain the compounds shown in Table 5.

TABLE 5

| Compounds | R¹ | R² | ¹H-NMR (CDCl$_3$) |
|---|---|---|---|
| Example 58 | H | H | δ1.68 (3H, d), 3.29 (3H, s), 4.82 (1H, q), 5.65 (1H, d), 6.87~7.60 (12H, m), 9.35 (1H, s) |
| Example 59 | H | F | δ1.68 (3H, d), 3.3 (3H, s), 4.85 (1H, q), 5.63 (1H, d), 6.93~7.60 (11H, m), 9.23 (1H, s) |
| Example 60 | CF$_3$ | F | δ1.68(3H, d), 3.7 (3H, s), 4.83 (1H, q), 6.87~7.60 (11H, m), 9.30 (1H, s) |
| Example 61 | H | CH$_3$ | δ1.68 (3H, d), 2.35 (3H, s), 3.29 (3H, s), 4.75 (1H, q), 5.66 (1H, d), 6.87~7.38 (11H, m), 9.35 (1H, s) |
| Example 62 | CF$_3$ | H | δ1.68 (3H, d), 3.63 (3H, s), 4.82 (1H, q), 6.87~7.60 (12H, m), 9.35 (1H, s) |
| Example 63 | H | Cl | δ1.69 (3H, d), 3.2 (3H, s), 4.85 (1H, q), 5.61 (1H, d), 6.93~7.59 (11H, m), 9.29 (1H, s) |
| Example 64 | CF$_3$ | Cl | δ1.69 (3H, d), 3.3 (3H, s), 4.82 (1H, q), 6.87~7.60 (12H, m), 9.35 (1H, s) |

Formulation Examples

Preparation of Herbicidal Formulations

Formulation Example 1

Wettable Powders

Wettable powders were prepared by thoroughly mixing the following components while spraying the liquid surfactant onto the solid components. The resulting mixture was firstly ground in a hammer mill to obtain the powder having an average particle size of 100 μm or less and, then, secondly ground in an air mill to obtain the powder having an average particle size of 10 μm or less.

Compounds of any one of Examples 1 to 15, 20 and 22 to 34: 20% by weight
Sodium lignin sulfonate: 4% by weight
Sodium silicon aluminate: 6% by weight
Dodecylphenol polyethylene glycol ether: 2% by weight
Montmorillonite: 68% by weight

Formulation Example 2

Water-Dispersible Granules

The procedure of Formulation Example 1 was repeated except for using the following components to obtain water-dispersible granules.

Compounds of any one of Examples 1 to 15, 20 and 22 to 34: 20% by weight
Sodium naphthalene sulfonate: 10% by weight
Sodium dodecyl sulfate: 2% by weight
Dicalite: 15% by weight
Calcium carbonate: 53% by weight

Formulation Example 3

Emulsions

Emulsions were prepared by mixing the following components, followed by homogeneously dissolving the mixture.

Compounds of any one of Examples 1 to 15, 20 and 22 to 34: 20% by weight
Polyoxyethylene octylphenylether: 11% by weight
Calcium alkylbenzene sulfonate: 4% by weight
Cyclohexanone: 20% by weight
Methylnaphthalene: 45% by weight

Formulation Example 4

Granules

Granules were prepared by mixing and grinding the following components, adding 18 to 20 parts by weight of water thereto based on the 100 parts by weight of the mixture, kneading the mixture, and granulating the resulting mixture to an average particle size of 14 to 32 meshes.

Compounds of any one of Examples 1 to 15, 20 and 22 to 34: 5% by weight
Sodium lignin sulfonate: 4% by weight
Carboxymethyl cellulose: 2% by weight
Sodium lauryl alcohol sulfate: 2% by weight
Postassium sulfate: 16% by weight
Calcium carbonate: 71% by weight

Formulation Example 5

Microemulsions

Microemulsions were prepared by dissolving the following components in the organic solvent and adding 26 parts by weight of water thereto based on 100 parts by weight of the mixture to homogeneously dissolve the mixture.

Compound of any one of Examples 1 to 15, 20 and 22 to 34: 20% by weight
polyoxyethylene glycol mono(tristyrylphenyl)ether: 12% by weight
polyoxyethylene propylene glycol mono(tristyrylphenyl) ether: 12% by weight
glycol ether: 30% by weight
distilled water: 26% by weight

Test Examples

Weed Control Test

Test Example 1

Seeds of rice, wheat, soy bean, barley, corn, common sorgum, barnyard grass, large crabgrass, creek grass, green foxtail and fall panicum were placed in sandy loam in 600 cm$^2$ pots and covered with soil. After keeping the pots in a greenhouse at 20 to 30° C. allowing growth of the plants to the 3-leaf stage of the barnyard grass, 2,000 l/ha of an emulsion obtained by diluting with water a mixture of 1 part by weight of a test compound, 5 parts by weight of acetone and 1 part by weight of an emulsifying agent (Tween 80, Junsei) was applied to the surface of the foliage of the plants. The plant damage at 10 days and 20 days after the foliage treatment was visually evaluated from the level of 1 to 100% by comparison with the untreated control:

| | |
|---|---|
| 0% | No herbicidal effect (identical to that of the control) |
| 20% | Slight herbicidal effect |
| 70% | Good herbicidal effect |
| 90% | Excellent herbicidal Effect |
| 100% | Full herbicidal effect (complete control of the weeds) |

The plants used in the Test Examples are shown in Table 6, and the herbicidal activity of the test compounds are shown in Tables 7 and 8 in comparison with a known herbicide, phenoxaprop-P-ethyl(Bayer CropScience GmbH):

TABLE 6

| Abbreviation | Scientific name | Common name |
|---|---|---|
| ZEAMX | *Zea mays* L. | corn |
| GLXMA | *Glycine max*(L.) MERR | soy bean |
| TRZAW | *Tritium aestivum* L. | wheat |
| ORYSA | *Oryza sativa* cv. Dongjin | rice |
| SORBI | *Andropogon sorghum* | common sorgum |
| HORVU | *Hordeum vulgare* L. | barley |
| ECHOG | *Echinoch crus-galli* Beauv. var. *caudata* Kitagawa | barnyard grass |
| DIGSA | *Digitaria Sanguinalis* (L.) SCOP | large crabgrass |
| PANDI | *Panium dichotomiflorum* Michx | fall panicum |
| ARTHIS | *Arthraxon hispidus* (Thunb.) Makino | creek grass |
| SETVIR | *Setaria viridis* (L.) Beauv | green foxtail |

TABLE 7

| Test compound (Example No.) | Plant name | Treatment Dosage(kg/ha) 0.2 | 0.1 | 0.025 |
|---|---|---|---|---|
| 1 | ZEAMX | 100 | 100 | 30 |
| | GLXMA | 0 | 0 | 0 |
| | TRZAW | 0 | 0 | 0 |
| | ORYSA | 0 | 0 | 0 |
| | SORBI | 100 | 100 | 60 |
| | HORVU | 0 | 0 | 0 |
| | ECHOG | 100 | 100 | 95 |
| | DIGSA | 100 | 100 | 90 |
| | PANDI | 100 | 100 | 90 |
| | ARTHIS | 100 | 100 | 70 |
| | SETVIR | 100 | 100 | 70 |
| 5 | ZEAMX | 100 | 100 | 60 |
| | GLXMA | 0 | 0 | 0 |
| | TRZAW | 0 | 0 | 0 |
| | ORYSA | 10 | 0 | 0 |
| | SORBI | 100 | 100 | 25 |
| | HORVU | 10 | 0 | 0 |
| | ECHOG | 100 | 100 | 95 |
| | DIGSA | 100 | 100 | 95 |
| | PANDI | 100 | 100 | 90 |
| | ARTHIS | 100 | 100 | 40 |
| | SETVIR | 100 | 100 | 80 |
| 6 | ZEAMX | 90 | 10 | 0 |
| | GLXMA | 0 | 0 | 0 |
| | TRZAW | 0 | 0 | 0 |
| | ORYSA | 0 | 0 | 0 |
| | SORBI | 90 | 50 | 10 |
| | HORVU | 70 | 0 | 0 |
| | ECHOG | 70 | 20 | 0 |
| | DIGSA | 70 | 20 | 0 |
| | PANDI | 70 | 20 | 0 |
| | ARTHIS | 50 | 20 | 0 |
| | SETVIR | 50 | 20 | 0 |
| 13 | ZEAMX | 100 | 100 | 40 |
| | GLXMA | 0 | 0 | 0 |
| | TRZAW | 0 | 0 | 0 |
| | ORYSA | 5 | 5 | 0 |
| | SORBI | 100 | 100 | 30 |
| | HORVU | 5 | 5 | 0 |
| | ECHOG | 100 | 100 | 70 |
| | DIGSA | 100 | 100 | 75 |
| | PANDI | 100 | 100 | 20 |
| | ARTHIS | 100 | 100 | 50 |
| | SETVIR | 100 | 100 | 50 |
| 14 | ZEAMX | 90 | 10 | 0 |
| | GLXMA | 0 | 0 | 0 |
| | TRZAW | 0 | 0 | 0 |
| | ORYSA | 0 | 0 | 0 |
| | SORBI | 90 | 50 | 10 |
| | HORVU | 70 | 0 | 0 |
| | ECHOG | 70 | 20 | 0 |
| | DIGSA | 70 | 20 | 0 |
| | PANDI | 70 | 20 | 0 |
| | ARTHIS | 50 | 20 | 0 |
| | SETVIR | 50 | 20 | 0 |
| 19 | ZEAMX | 30 | 10 | 0 |
| | GLXMA | 0 | 0 | 0 |
| | TRZAW | 0 | 0 | 0 |
| | ORYSA | 0 | 0 | 0 |
| | SORBI | 70 | 60 | 20 |
| | HORVU | 0 | 0 | 0 |
| | ECHOG | 30 | 20 | 0 |
| | DIGSA | 30 | 10 | 0 |
| | PANDI | 0 | 0 | 0 |
| | ARTHIS | 10 | 10 | 0 |
| | SETVIR | 10 | 10 | 0 |
| 21 | ZEAMX | 100 | 90 | 20 |
| | GLXMA | 0 | 0 | 0 |
| | TRZAW | 0 | 0 | 0 |
| | ORYSA | 0 | 0 | 0 |
| | SORBI | 50 | 20 | 0 |
| | HORVU | 0 | 0 | 0 |
| | ECHOG | 90 | 70 | 20 |
| | DIGSA | 90 | 20 | 0 |
| | PANDI | 70 | 70 | 0 |
| | ARTHIS | 70 | 70 | 0 |
| | SETVIR | 90 | 70 | 0 |
| 23 | ZEAMX | 90 | 90 | 10 |
| | GLXMA | 0 | 0 | 0 |
| | TRZAW | 0 | 0 | 0 |
| | ORYSA | 0 | 0 | 0 |
| | SORBI | 20 | 20 | 0 |
| | HORVU | 0 | 0 | 0 |
| | ECHOG | 50 | 50 | 20 |
| | DIGSA | 20 | 20 | 0 |
| | PANDI | 10 | 0 | 0 |
| | ARTHIS | 10 | 0 | 0 |
| | SETVIR | 20 | 0 | 0 |
| 26 | ZEAMX | 30 | 10 | 10 |
| | GLXMA | 0 | 0 | 0 |
| | TRZAW | 0 | 0 | 0 |
| | ORYSA | 0 | 0 | 0 |
| | SORBI | 35 | 20 | 10 |
| | HORVU | 0 | 0 | 0 |
| | ECHOG | 0 | 0 | 0 |
| | DIGSA | 0 | 0 | 0 |
| | PANDI | 0 | 0 | 0 |
| | ARTHIS | 0 | 0 | 0 |
| | SETVIR | 0 | 0 | 0 |
| 27 | ZEAMX | 90 | 90 | 10 |
| | GLXMA | 0 | 0 | 0 |
| | TRZAW | 0 | 0 | 0 |
| | ORYSA | 20 | 0 | 0 |
| | SORBI | 20 | 20 | 0 |
| | HORVU | 0 | 0 | 0 |
| | ECHOG | 90 | 70 | 20 |
| | DIGSA | 90 | 20 | 0 |
| | PANDI | 10 | 0 | 0 |
| | ARTHIS | 10 | 0 | 0 |
| | SETVIR | 20 | 0 | 0 |
| 29 | ZEAMX | 30 | 5 | 0 |
| | GLXMA | 0 | 0 | 0 |
| | TRZAW | 0 | 0 | 0 |
| | ORYSA | 0 | 0 | 0 |
| | SORBI | 50 | 20 | 0 |
| | HORVU | 0 | 0 | 0 |
| | ECHOG | 90 | 70 | 20 |
| | DIGSA | 90 | 20 | 0 |
| | PANDI | 10 | 0 | 0 |
| | ARTHIS | 10 | 0 | 0 |
| | SETVIR | 20 | 0 | 0 |
| 31 | ZEAMX | 90 | 90 | 20 |
| | GLXMA | 0 | 0 | 0 |
| | TRZAW | 0 | 0 | 0 |
| | ORYSA | 0 | 0 | 0 |
| | SORBI | 50 | 20 | 0 |
| | HORVU | 0 | 0 | 0 |
| | ECHOG | 90 | 50 | 0 |
| | DIGSA | 70 | 20 | 0 |
| | PANDI | 20 | 20 | 0 |
| | ARTHIS | 70 | 70 | 0 |
| | SETVIR | 70 | 70 | 0 |
| 35 | ZEAMX | 30 | 20 | 0 |
| | GLXMA | 0 | 0 | 0 |
| | TRZAW | 0 | 0 | 0 |
| | ORYSA | 0 | 0 | 0 |
| | SORBI | 80 | 65 | 20 |
| | HORVU | | 0 | 0 |
| | ECHOG | 30 | 10 | 0 |
| | DIGSA | 60 | 40 | 10 |
| | PANDI | 30 | 0 | 0 |
| | ARTHIS | 30 | 10 | 0 |
| | SETVIR | 50 | 30 | 0 |
| 37 | ZEAMX | 30 | 0 | 0 |
| | GLXMA | 0 | 0 | 0 |
| | TRZAW | 0 | 0 | 0 |
| | ORYSA | 0 | 0 | 0 |
| | SORBI | 20 | 20 | 0 |
| | HORVU | 0 | 0 | 0 |
| | ECHOG | 90 | 70 | 20 |
| | DIGSA | 90 | 20 | 0 |
| | PANDI | 10 | 0 | 0 |

TABLE 7-continued

| Test compound (Example No.) | Plant name | Treatment Dosage(kg/ha) | | |
|---|---|---|---|---|
| | | 0.2 | 0.1 | 0.025 |
| | ARTHIS | 10 | 0 | 0 |
| | SETVIR | 20 | 0 | 0 |
| 40 | ZEAMX | 100 | 100 | 90 |
| | GLXMA | 0 | 0 | 0 |
| | TRZAW | 0 | 0 | 0 |
| | ORYSA | 0 | 0 | 0 |
| | SORBI | 50 | 20 | 0 |
| | HORVU | 0 | 0 | 0 |
| | ECHOG | 90 | 70 | 20 |
| | DIGSA | 90 | 90 | 70 |
| | PANDI | 10 | 0 | 0 |
| | ARTHIS | 10 | 0 | 0 |
| | SETVIR | 20 | 0 | 0 |
| 41 | ZEAMX | 20 | 0 | 0 |
| | GLXMA | 0 | 0 | 0 |
| | TRZAW | 0 | 0 | 0 |
| | ORYSA | 0 | 0 | 0 |
| | SORBI | 0 | 0 | 0 |
| | HORVU | 0 | 0 | 0 |
| | ECHOG | 20 | 0 | 0 |
| | DIGSA | 50 | 0 | 0 |
| | PANDI | 70 | 70 | 20 |
| | ARTHIS | 20 | 0 | 0 |
| | SETVIR | 70 | 20 | 0 |
| 42 | ZEAMX | 90 | 30 | 0 |
| | GLXMA | 0 | 0 | 0 |
| | TRZAW | 0 | 0 | 0 |
| | ORYSA | 0 | 0 | 0 |
| | SORBI | 0 | 0 | 0 |
| | HORVU | 0 | 0 | 0 |
| | ECHOG | 20 | 20 | 0 |
| | DIGSA | 20 | 0 | 0 |
| | PANDI | 70 | 0 | 0 |
| | ARTHIS | 50 | 0 | 0 |
| | SETVIR | 70 | 0 | 0 |
| 52 | ZEAMX | 30 | 30 | 10 |
| | GLXMA | 0 | 0 | 0 |
| | TRZAW | 0 | 0 | 0 |
| | ORYSA | 50 | 20 | 0 |
| | SORBI | 0 | 0 | 0 |
| | HORVU | 0 | 0 | 0 |
| | ECHOG | 20 | 0 | 0 |
| | DIGSA | 10 | 0 | 0 |
| | PANDI | 0 | 0 | 0 |
| | ARTHIS | 0 | 0 | 0 |
| | SETVIR | 10 | 0 | 0 |
| 55 | ZEAMX | 30 | 10 | 10 |
| | GLXMA | 0 | 0 | 0 |
| | TRZAW | 0 | 0 | 0 |
| | ORYSA | 0 | 0 | 0 |
| | SORBI | 35 | 20 | 10 |
| | HORVU | 0 | 0 | 0 |
| | ECHOG | 0 | 0 | 0 |
| | DIGSA | 0 | 0 | 0 |
| | PANDI | 0 | 0 | 0 |
| | ARTHIS | 0 | 0 | 0 |
| | SETVIR | 0 | 0 | 0 |
| 56 | ZEAMX | 90 | 90 | 10 |
| | GLXMA | 0 | 0 | 0 |
| | TRZAW | 0 | 0 | 0 |
| | ORYSA | 0 | 0 | 0 |
| | SORBI | 20 | 20 | 0 |
| | HORVU | 0 | 0 | 0 |
| | ECHOG | 90 | 70 | 20 |
| | DIGSA | 90 | 20 | 0 |
| | PANDI | 10 | 0 | 0 |
| | ARTHIS | 10 | 0 | 0 |
| | SETVIR | 20 | 0 | 0 |
| Phenoxaprop-P-ethyl | ZEAMX | 100 | 100 | 30 |
| | GLXMA | 0 | 0 | 0 |
| | TRZAW | 10 | 10 | 0 |
| | ORYSA | 0 | 0 | 0 |
| | SORBI | 100 | 100 | 50 |
| | HORVU | 40 | 20 | 0 |
| | ECHOG | 100 | 100 | 30 |
| | DIGSA | 100 | 100 | 40 |
| | PANDI | 100 | 100 | 30 |
| | ARTHIS | 100 | 100 | 30 |
| | SETVIR | 100 | 100 | 20 |

TABLE 8

| Test compound (Example No.) | 4-leaf stage Plants | Treatment Dosage (kg/ha) | | | |
|---|---|---|---|---|---|
| | | 0.4 | 0.1 | 0.05 | 0.025 |
| 1 | Rice | 0 | 0 | 0 | 0 |
| | Barnyard grass | 100 | 100 | 90 | 70 |
| 5 | Rice | 0 | 0 | 0 | 0 |
| | Barnyard grass | 100 | 100 | 95 | 70 |
| 6 | Rice | 0 | 0 | 0 | 0 |
| | Barnyard grass | 30 | 10 | 0 | 0 |
| 13 | Rice | 20 | 0 | 0 | 0 |
| | Barnyard grass | 100 | 70 | 50 | 20 |
| 14 | Rice | 0 | 0 | 0 | 0 |
| | Barnyard grass | 50 | 10 | 0 | 0 |
| 33 | Rice | 20 | 0 | 0 | 0 |
| | Barnyard grass | 100 | 100 | 40 | 10 |
| Phenoxaprop-P-ethyl | Rice | 80 | 70 | 30 | 20 |
| | Barnyard grass | 100 | 100 | 100 | 90 |

As can be seen in Tables 7 and 8, the compounds prepared in the Examples exhibit high selectivity and safety for crop plants, while exhibiting excellent herbicidal activity against undesired weed grasses.

Test Example 2

Seeds of rice (Nampyung rice) and barnyard grasses (*Echinochloa oryzicola* and *Echinochloa crus-galli* var. *crus-galli*) were placed in sandy loam of pots, covered with soil, and grown in the dry rice field conditions.

Rice (6~6.5-leaf stage, plant height 33.2 cm) and barnyard grasses (*Echinochloa oryzicola*: division stage 1~2, plant height 38.0 cm, *Echinochloa crus-galli* var. *crus-galli*: division stage 1~2, plant height 44.1 cm) were subjected to a foliage treatment with emulsions prepared according to Formulation Example 3 by using compounds of Examples 1, 5 and 13 (purity: 99% or more), wherein the emulsions were sprayed to the plants at a dosage of the active compound of 150 g/ha.

The herbicidal effect on the barnyard grasses and harmful effect on the rice of the test compounds at 20 days and 30 days after the foliage treatment were visually evaluated as in Test Example 1 in comparison with the untreated control, and the results are shown in Table 9.

TABLE 9

| Test compound (Example No.) | Amount (g a.i./ ha) | Herbicidal effect (0~100), 20 days | | Harmful effect | |
|---|---|---|---|---|---|
| | | Echinochloa oryzicola | Echinochloa crus-galli var. crus-galli | 20 days | 30 days |
| 1 | 150 | 100 | 100 | 0 | 0 |
| 5 | 150 | 100 | 100 | 0 | 0 |
| 13 | 150 | 70 | 80 | 10 | 0 |
| Phenoxaprop-P-ethyl | 150 | 100 | 100 | 23 | 38 |

As can be seen in Table 9, the inventive (R)-aryloxypropionic acid amide compounds prepared in the Examples exhibit excellent herbicidal effects on *Echinochloa oryzicola* and *Echinochloa crus-galli* var. *crus-galli* at 20 days after the foliage treatment, as compared with the comparative compound, phenoxaprop-P-ethyl.

What is claimed is:

1. An optically active (R)-aryloxypropionic acid amide compound of formula (I):

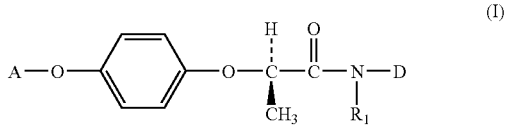

wherein,
A is fluorophenylvinyl, cyanofluorophenyl or chlorobenzoxazolyl, optionally substituted with one or more substituents each independently selected from the group consisting of $CF_3$, halogen and $C_{1-4}$ alkyl;
D is benzoxazolyl, benzothiazolyl, or benzimidazolyl, optionally substituted with one or more substituents each independently selected from the group consisting of halogen, $C_{1-4}$ alkyl and $C_{1-4}$ alkoxy; and
$R_1$ is hydrogen or $C_{1-4}$ alkyl.

2. The compound of claim 1, wherein A is 1-fluoro-2-phenylvinyl, 1-fluoro-2-(4-fluorophenyl)vinyl, 1,3,3,3-tetrafluoro-2-phenylpropen-1-yl, 1,3,3,3-tetrafluoro-2-(4-fluorophenyl)propen-1-yl, 1-fluoro-2-(4-methyl-phenyl)vinyl, 1-fluoro-2-(4-chlorophenyl)vinyl, 1,3,3,3-tetrafluoro-2-(4-chlorophenyl)propen-1-yl, 6-chlorobenzoxazolyl or 4-cyano-2-fluorophenyl; D is 5-chloro-2-benzoxazolyl, 1-methyl-2-benzimidazolyl, 2-benzthiazolyl, 6-chloro-2-benzthiazolyl, 6-fluoro-2-benzthiazolyl, 6-methyl-2-benzthiazolyl, 6-methoxy-2-benzthiazolyl, or 5-chloro-2-benzoxazolyl; and $R_1$ is hydrogen or methyl.

3. The compound of claim 1, which is selected from the group consisting of:
(1) (R)-2-[4-(6-chloro-2-benzoxazolyloxy)phenoxy]propionic acid-N-(5-chloro-2-benzoxazolyl)amide;
(2) (R)-2-[4-(6-chloro-2-benzoxazolyloxy)phenoxy]propionic acid-N-(5-chloro-2-benzoxazolyl)-N-methyl amide;
(3) (R)-2-[4-(6-chloro-2-benzoxazolyloxy)phenoxy]propionic acid-N-(1-methyl-2-benzimidazolyl)amide;
(4) (R)-2-[4-(6-chloro-2-benzoxazolyloxy)phenoxy]propionic acid-N-(1-methyl-2-benzimidazolyl)-N-methyl amide;
(5) (R)-2-[4-(6-chloro-2-benzoxazolyloxy)phenoxy]propionic acid-N-(2-benzothiazolyl)amide;
(6) (R)-2-[4-(6-chloro-2-benzoxazolyloxy)phenoxy]propionic acid-N-(2-benzothiazolyl)-N-methyl amide;
(7) (R)-2-[4-(6-chloro-2-benzoxazolyloxy)phenoxy]propionic acid-N-(6-chloro-2-benzothiazolyl)amide;
(8) (R)-2-[4-(6-chloro-2-benzoxazolyloxy)phenoxy]propionic acid-N-(6-chloro-2-benzothiazolyl)-N-methyl amide;
(9) (R)-2-[4-(6-chloro-2-benzoxazolyloxy)phenoxy]propionic acid-N-(6-fluoro-2-benzothiazolyl)amide;
(10) (R)-2-[4-(6-chloro-2-benzoxazolyloxy)phenoxy]propionic acid-N-(6-fluoro-2-benzothiazolyl)-N-methyl amide;
(11) (R)-2-[4-(6-chloro-2-benzoxazolyloxy)phenoxy]propionic acid-N-(6-methyl-2-benzothiazolyl)amide;
(12) (R)-2-[4-(6-chloro-2-benzoxazolyloxy)phenoxy]propionic acid-N-(6-methyl-2-benzothiazolyl)-N-methyl amide;
(13) (R)-2-[4-(6-chloro-2-benzoxazolyloxy)phenoxy]propionic acid-N-(6-methoxy-2-benzothiazolyl)amide;
(14) (R)-2-[4-(6-chloro-2-benzoxazolyloxy)phenoxy]propionic acid-N-(6-methoxy-2-benzothiazolyl)-N-methyl amide;
(15) (R)-2-[4-(4-cyano-2-fluorophenoxy)phenoxy]propionic acid-N-(5-chloro-2-benzoxazolyl)amide;
(16) (R)-2-[4-(4-cyano-2-fluorophenoxy)phenoxy]propionic acid-N-(5-chloro-2-benzoxazolyl)-N-methyl amide;
(17) (R)-2-[4-(4-cyano-2-fluorophenoxy)phenoxy]propionic acid-N-(1-methyl-2-benzimidazolyl)amide;
(18) (R)-2-[4-(4-cyano-2-fluorophenoxy)phenoxy]propionic acid-N-(1-methyl-2-benzimidazolyl)-N-methyl amide;
(19) (R)-2-[4-(4-cyano-2-fluorophenoxy)phenoxy]propionic acid-N-(2-benzothiazolyl)amide;
(20) (R)-2-[4-(4-cyano-2-fluorophenoxy)phenoxy]propionic acid-N-(2-benzothiazolyl)-N-methyl amide;
(21) (R)-2-[4-(4-cyano-2-fluorophenoxy)phenoxy]propionic acid-N-(6-chloro-2-benzothiazolyl)amide;
(22) (R)-2-[4-(4-cyano-2-fluorophenoxy)phenoxy]propionic acid-N-(6-chloro-2-benzothiazolyl)-N-methyl amide;
(23) (R)-2-[4-(4-cyano-2-fluorophenoxy)phenoxy]propionic acid-N-(6-fluoro-2-benzothiazolyl)amide;
(24) (R)-2-[4-(4-cyano-2-fluorophenoxy)phenoxy]propionic acid-N-(6-fluoro-2-benzothiazolyl)-N-methyl amide;
(25) (R)-2-[4-(4-cyano-2-fluorophenoxy)phenoxy]propionic acid-N-(6-methyl-2-benzothiazolyl)amide;
(26) (R)-2-[4-(4-cyano-2-fluorophenoxy)phenoxy]propionic acid-N-(6-methyl-2-benzothiazolyl)-N-methyl amide;
(27) (R)-2-[4-(4-cyano-2-fluorophenoxy)phenoxy]propionic acid-N-(6-methoxy-2-benzothiazolyl)amide;
(28) (R)-2-[4-(4-cyano-2-fluorophenoxy)phenoxy]propionic acid-N-(6-methoxy-2-benzothiazolyl)-N-methyl amide;
(51) (R)-2-[4-(1-fluoro-2-phenylvinyloxy)phenoxy]propionic acid-N-(5-chloro-2-benzoxazolyl)amide;
(52) (R)-2-[4-(1-fluoro-2-(4-fluorophenyl)vinyloxy)phenoxy]propionic acid-N-(5-chloro-2-benzoxazolyl)amide;
(53) (R)-2-[4-(1,3,3,3-tetrafluoro-2-(4-fluorophenyl)prop-1-enyl)phenoxy]propionic acid-N-(5-chloro-2-benzoxazolyl)amide;
(54) (R)-2-[4-(1-fluoro-2-(4-methylphenyl)vinyloxy)phenoxy]propionic acid-N-(5-chloro-2-benzoxazolyl)amide;

(55) (R)-2-[4-(1,3,3,3-tetrafluoro-2-phenylprop-1-enyl)phenoxy]propionic acid-N-(5-chloro-2-benzoxazolyl) amide;
(56) (R)-2-[4-(1-fluoro-2-(4-chlorophenyl)vinyloxy)phenoxy]propionic acid-N-(5-chloro-2-benzoxazolyl) amide;
(57) (R)-2-[4-(1,3,3,3-tetrafluoro-2-(4-chlorophenyl)prop-1-enyl)phenoxy]propionic acid-N-(5-chloro-2-benzoxazolyl)amide;
(58) (R)-2-[4-(1-fluoro-2-phenylvinyloxy)phenoxy]propionic acid-N-(5-chloro-2-benzoxazolyl)-N-methyl amide;
(59) (R)-2-[4-(1-fluoro-2-(4-fluorophenyl)vinyloxy)phenoxy]propionic acid-N-(5-chloro-2-benzoxazolyl)-N-methyl amide;
(60) (R)-2-[4-(1,3,3,3-tetrafluoro-2-(4-fluorophenyl)prop-1-enyl)phenoxy]propionic acid-N-(5-chloro-2-benzoxazolyl)-N-methyl amide;
(61) (R)-2-[4-(1-fluoro-2-(4-methylphenyl)vinyloxy)phenoxy]propionic acid-N-(5-chloro-2-benzoxazolyl)-N-methyl amide;
(62) (R)-2-[4-(1,3,3,3-tetrafluoro-2-phenylprop-1-enyl)phenoxy]propionic acid-N-(5-chloro-2-benzoxazolyl)-N-methyl amide;
(63) (R)-2-[4-(1-fluoro-2-(4-chlorophenyl)vinyloxy)phenoxy]propionic acid-N-(5-chloro-2-benzoxazolyl)-N-methyl amide; and
(64) (R)-2-[4-(1,3,3,3-tetrafluoro-2-(4-chlorophenyl)prop-1-enyl)phenoxy]propionic acid-N-(5-chloro-2-benzoxazolyl)-N-methyl amide.

4. A method for preparing the optically active (R)-aryloxypropionic acid amide compound of formula (I) of claim 1, which comprises subjecting a compound of formula (VI) to a reaction with a compound of formula (VII):

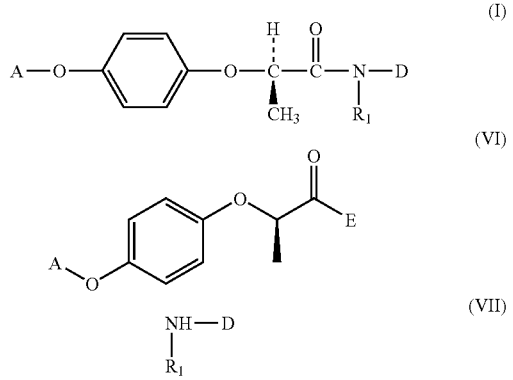

wherein,
A is fluorophenylvinyl, cyanofluorophenyl or chlorobenzoxazolyl, optionally substituted with one or more substituents each independently selected from the group consisting of $CF_3$, halogen and $C_{1-4}$ alkyl;
D is benzoxazolyl, benzothiazolyl, or benzimidazolyl, each optionally substituted with one or more substituents each independently selected from the group consisting of halogen, $C_{1-4}$ alkyl and $C_{1-4}$ alkoxy;
$R_1$ is hydrogen or $C_{1-4}$ alkyl; and
E is OH, Cl, Br or phenoxy.

5. The method of claim 4, wherein the reaction is carried out at a temperature ranging from −10 to 100° C. in the presence of an organic base.

6. A method for preparing the optically active (R)-aryloxypropionic acid amide compound of formula (I) of claim 1, which comprises subjecting a compound of formula (VIII) to a reaction with a compound of formula (IX):

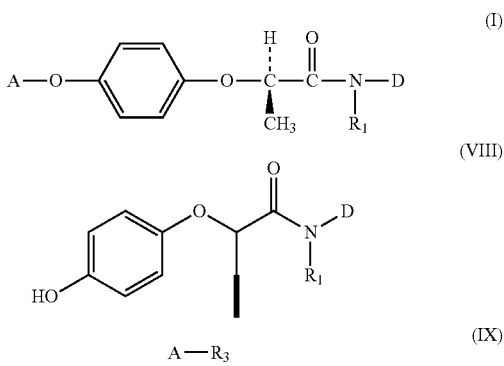

wherein,
A is fluorophenylvinyl, cyanofluorophenyl or chlorobenzoxazolyl, optionally substituted with one or more substituents each independently selected from the group consisting of $CF_3$, halogen and $C_{1-4}$ alkyl;
D is benzoxazolyl, benzothiazolyl, or benzimidazolyl, each optionally substituted with one or more substituents each independently selected from the group consisting of halogen, $C_{1-4}$ alkyl and $C_{1-4}$ alkoxy;
$R_1$ is hydrogen or $C_{1-4}$ alkyl; and
$R_3$ is hydrogen, halogen or $C_{1-4}$ alkyl.

7. The method of claim 6, wherein the reaction is carried out at a temperature ranging from 20 to 150° C. in the presence of an inorganic or organic base.

8. A herbicidal composition comprising the optically active (R)-aryloxypropionic acid amide compound of claim 1 as an active ingredient.

9. The herbicidal composition of claim 8, which further comprises one or more agriculturally acceptable additives.

* * * * *